(12) United States Patent
Litvak et al.

(10) Patent No.: US 12,357,186 B2
(45) Date of Patent: Jul. 15, 2025

(54) SYSTEMS AND METHODS FOR MONITORING AND ACTING ON A PHYSIOLOGICAL CONDITION OF A STIMULATION SYSTEM RECIPIENT

(71) Applicant: Advanced Bionics AG, Staefa (CH)

(72) Inventors: Leonid M. Litvak, Los Angeles, CA (US); R. Tissa Karunasiri, Valencia, CA (US); Hannah A. Glick, Ventura, CA (US); Kanthaiah Koka, Valencia, CA (US); Chen Chen, Valencia, CA (US); Anthony J. Spahr, Newhall, CA (US); Jason Galster, Studio City, CA (US); Dean Swan, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 501 days.

(21) Appl. No.: 17/762,942

(22) PCT Filed: Oct. 23, 2020

(86) PCT No.: PCT/US2020/057175
§ 371 (c)(1),
(2) Date: Mar. 23, 2022

(87) PCT Pub. No.: WO2021/081412
PCT Pub. Date: Apr. 29, 2021

(65) Prior Publication Data
US 2022/0330844 A1 Oct. 20, 2022

Related U.S. Application Data

(60) Provisional application No. 62/926,350, filed on Oct. 25, 2019.

(51) Int. Cl.
*H04R 25/00* (2006.01)
*A61B 5/00* (2006.01)
(Continued)

(52) U.S. Cl.
CPC ........ *A61B 5/02405* (2013.01); *A61B 5/0022* (2013.01); *A61B 5/1116* (2013.01);
(Continued)

(58) Field of Classification Search
CPC .... A61B 2562/0204; A61B 2562/0219; A61B 5/0022; A61B 5/0205; A61B 5/02405;
(Continued)

(56) References Cited

U.S. PATENT DOCUMENTS 11,607,176 B2 * 3/2023 Brockway .............. A61B 5/318
2007/0225767 A1 9/2007 Daly et al.
(Continued)

OTHER PUBLICATIONS

"International Search Report and Written Opinion in International Application No. PCT/US2020/057175.".

*Primary Examiner* — Phylesha Dabney
(74) *Attorney, Agent, or Firm* — ALG Intellectual Property, LLC

(57) ABSTRACT

An illustrative system includes a stimulation device configured to apply stimulation to a recipient, a sensing device configured to detect a physiological condition of the recipient, and a processing unit communicatively coupled to the stimulation device and the sensing device. The processing unit determines a stimulation strategy that is customized to the recipient and includes stimulation frames and stimulation gaps. The processing unit then directs the stimulation device to apply the stimulation to the recipient in accordance with the stimulation strategy by applying the stimulation only during time that corresponds to the stimulation frames. The processing unit also directs the sensing device to detect the physiological condition of the recipient in accordance with the stimulation strategy by detecting only during time that corresponds to the stimulation gaps. Based on the detected physiological condition, the processing unit per-
(Continued)

forms an action. Corresponding systems, methods, and apparatuses are also disclosed.

14 Claims, 10 Drawing Sheets

(51) Int. Cl.
*A61B 5/024* (2006.01)
*A61B 5/11* (2006.01)
*A61B 5/16* (2006.01)
*A61B 5/347* (2021.01)
*A61B 5/372* (2021.01)
*A61B 5/389* (2021.01)
*A61B 5/398* (2021.01)
*A61B 5/0205* (2006.01)

(52) U.S. Cl.
CPC .............. *A61B 5/165* (2013.01); *A61B 5/347* (2021.01); *A61B 5/372* (2021.01); *A61B 5/389* (2021.01); *A61B 5/398* (2021.01); *A61B 5/4094* (2013.01); *A61B 5/4815* (2013.01); *A61B 5/4848* (2013.01); *A61B 5/6803* (2013.01); *A61B 5/0205* (2013.01)

(58) Field of Classification Search
CPC ... A61B 5/0261; A61B 5/1103; A61B 5/1116; A61B 5/1455; A61B 5/165; A61B 5/346; A61B 5/347; A61B 5/372; A61B 5/389; A61B 5/398; A61B 5/4094; A61B 5/4815; A61B 5/4848; A61B 5/6803; A61B 5/7203; A61B 5/746
USPC ........................................................ 381/312
See application file for complete search history.

(56) References Cited

U.S. PATENT DOCUMENTS

| | | |
|---|---|---|
| 2008/0097553 A1 | 4/2008 | John |
| 2008/0275347 A1* | 11/2008 | Takala .................. A61B 5/318 |
| | | 600/483 |
| 2013/0090517 A1 | 4/2013 | Van Den Heuvel |
| 2022/0054090 A1* | 2/2022 | Brockway ............... A61B 5/33 |
| 2024/0057945 A1* | 2/2024 | Brockway ............ A61B 5/7217 |

* cited by examiner

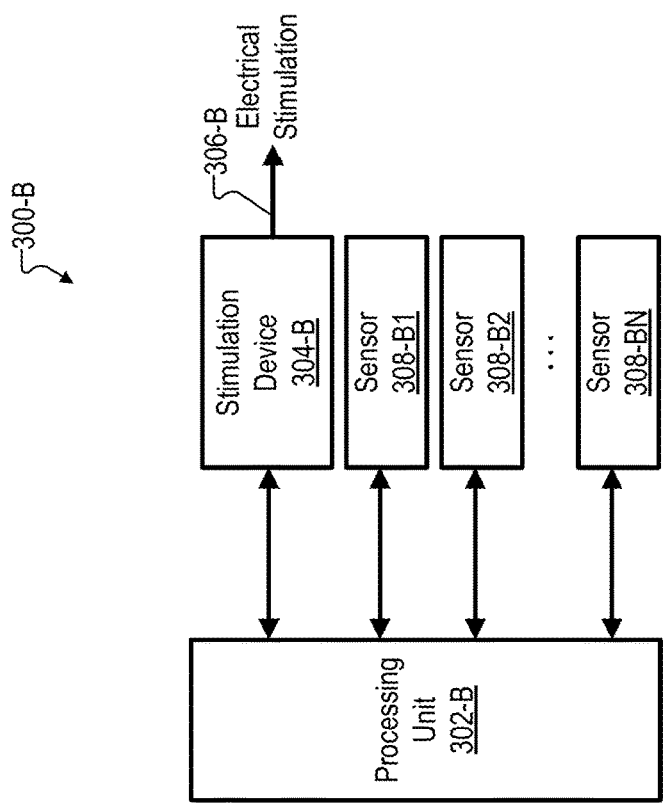
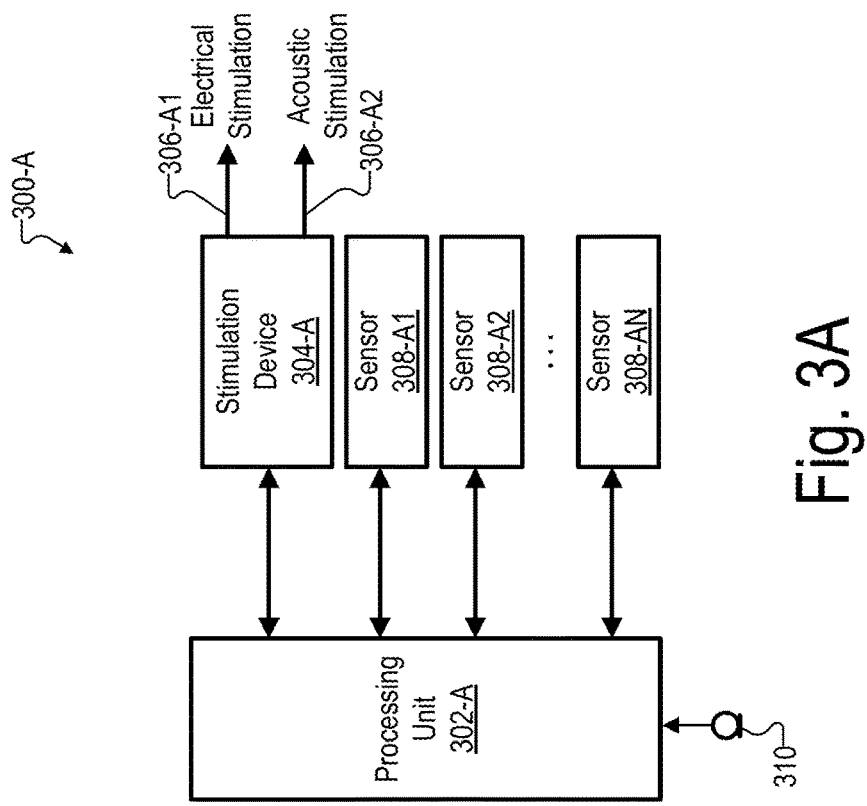
Fig. 3B
Fig. 3A

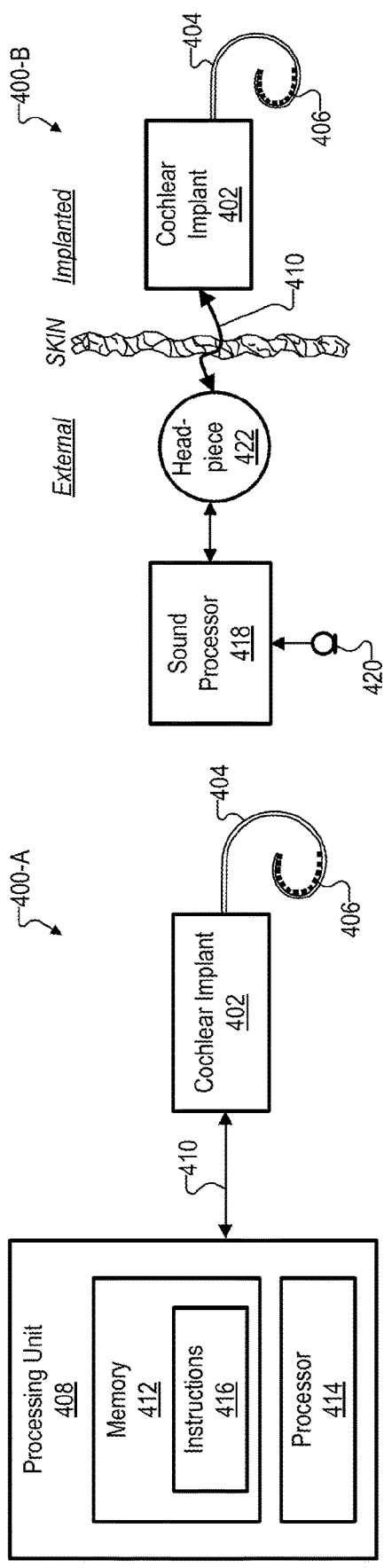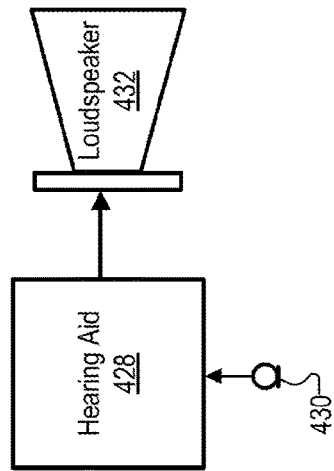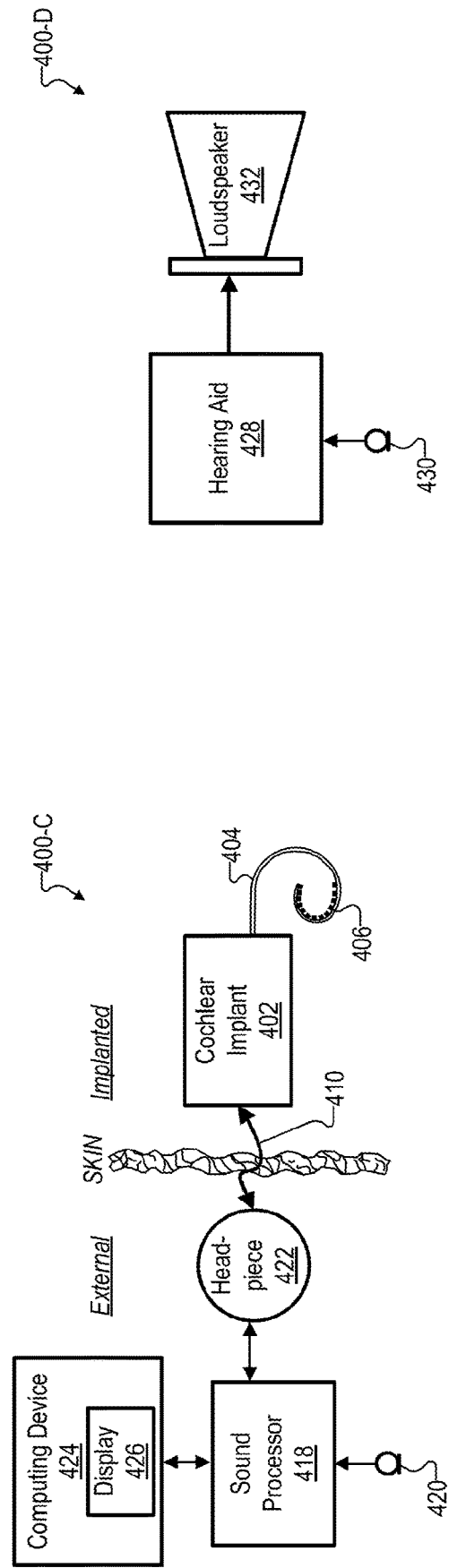
Fig. 4A
Fig. 4B
Fig. 4C
Fig. 4D

SYSTEMS AND METHODS FOR MONITORING AND ACTING ON A PHYSIOLOGICAL CONDITION OF A STIMULATION SYSTEM RECIPIENT

RELATED APPLICATIONS

The present application claims priority under 35 U.S.C. § 119(e) to U.S. Provisional Patent Application No. 62/926,350, filed on Oct. 25, 2019, and entitled "HEALTH AND/OR SENTIMENT MONITORING USING A HEARING SYSTEM, AND APPLICATIONS THEREOF," the contents of which are hereby incorporated by reference in their entirety.

BACKGROUND INFORMATION

Various types of stimulation systems (e.g., hearing systems, neuromodulation systems, etc.) are in use today by stimulation system recipients with many different capabilities and conditions. For example, people who are hard of hearing but retain basic hearing capabilities in one or both ears may use a hearing aid system for one or both ears. As another example, people who have little or no natural hearing may benefit from a cochlear implant system that stimulates auditory nerves in ways that natural hearing mechanisms fail to do for various reasons. In still other examples, people who suffer from chronic pain or other conditions may be treated using a neuromodulation system such as a spinal cord stimulation system or the like.

Regardless of which of these or other types of stimulation systems a particular recipient may use, it may be desirable for a stimulation system to operate in a manner that is catered to the recipient's own unique preferences and characteristics.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 3A-3B show illustrative implementations of the stimulation system of FIG. 1.

FIGS. 4A-4D show illustrative implementations of the hearing system of FIG. 3A.

DETAILED DESCRIPTION

Figure 1:
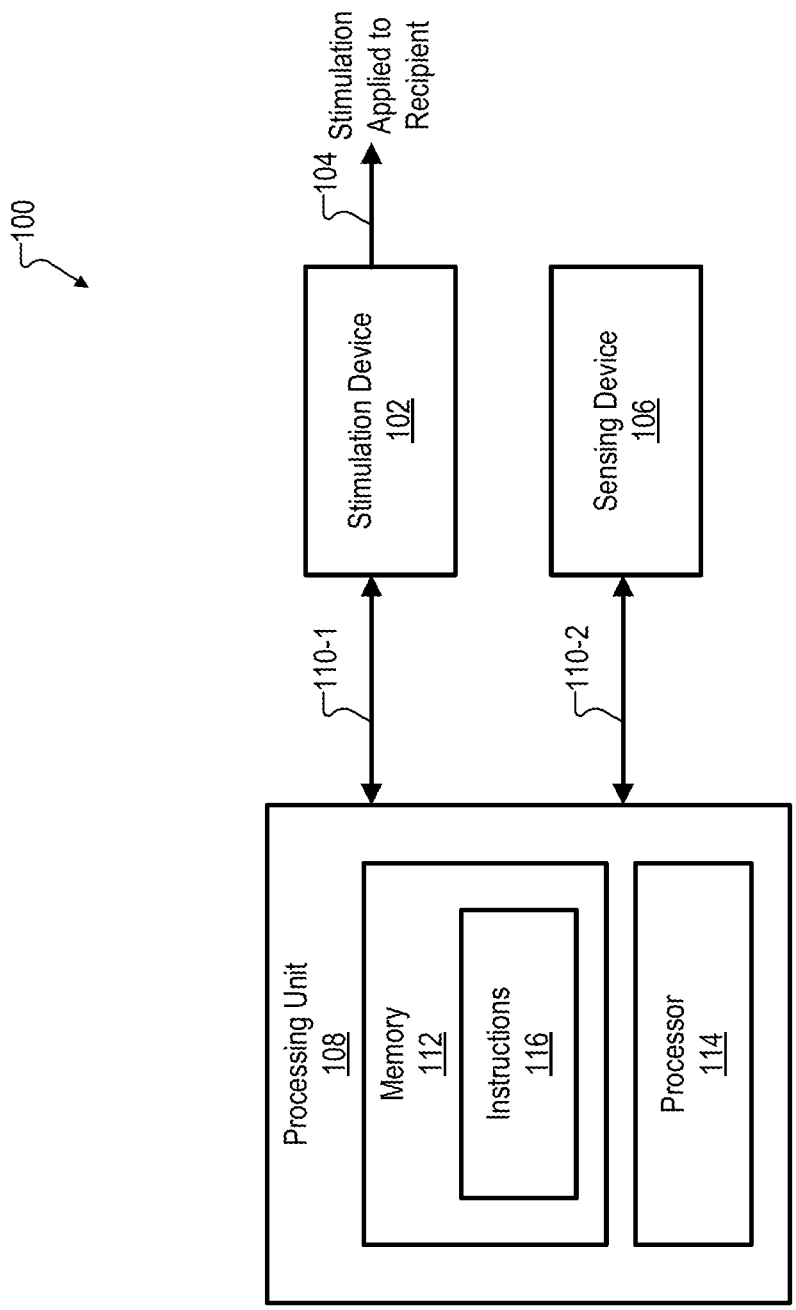
FIG. 1 shows an illustrative stimulation system configured to monitor and act on a physiological condition of a recipient.

Systems and methods for monitoring and acting on a physiological condition of a stimulation system recipient are described herein. As used herein, a stimulation system "recipient" may refer to any person who wears, has implanted, or otherwise directly uses (e.g., received stimulation from) a stimulation system such as those stimulation systems described herein. For example, a recipient may refer to person who has been implanted with a cochlear implant or neuromodulator system, a person who wears a hearing aid, earphone, or other type of hearing system, or any other person who directly uses a stimulation system in these ways. In contrast, as used herein, "users" of a stimulation system may refer to either the recipients themselves or, more broadly, to others who may use the system in some capacity without actually wearing the system, being implanted with the system, or otherwise receiving stimulation from the system. For example, along with recipients themselves, other users of a stimulation system may include caretakers (e.g., parents, guardians, etc.) of the recipients, clinicians or other healthcare providers overseeing care of the recipients with respect to the stimulation system, and so forth.

Certain stimulation system recipients may suffer in various degrees from various types of conditions. Regardless of what type or degree of stimulation a particular recipient may receive from a given stimulation system, however, it may be desirable for the stimulation system to be customized for various unique preferences and/or characteristics of the recipient. To this end, systems and methods described herein may monitor and act on physiological conditions of recipients. For example, systems and methods described herein may be configured to account for and be responsive to various real-time physiological conditions that will be described herein. Without limitation, such physiological conditions may include, for instance, health conditions (e.g., a heart rate variability of the recipient, the occurrence of an episode of a pathologic condition of the recipient, etc.), sentiment conditions (e.g., a stress level of the recipient, a quality of sleep the recipient is engaged in, etc.), real-time behavioral conditions (e.g., a direction that the recipient is looking, an attentiveness level of the recipient with respect to his or her environment, etc.), and so forth. Physiological conditions may be associated with any of the biometrics described herein that may be measured, recorded, monitored, or otherwise detected in any of the ways and/or using any of the sensing devices that will be described.

As systems described herein identify and monitor physiological conditions of a recipient using any of various sensors and/or tests described herein, the systems may be configured to act on the detected physiological conditions in various ways. For example, the systems may alert or notify the recipient of the physiological condition or information derived therefrom, store or present the physiological condition, analyze the physiological condition, adjust system parameters, or otherwise use the physiological condition to improve the stimulation system's operation or performance, to improve the recipient's experience (e.g., to treat a condition the recipient suffers from, to enable the recipient to hear or improve his or her hearing, etc.), to assist a caregiver of the recipient, or to otherwise improve or enable the experience provided to the recipient by the stimulation system.

Systems and methods described herein for monitoring and acting on a physiological condition of a recipient may significantly improve stimulation system technology and provide technical benefits to the system, while also providing usability benefits and advantages to recipients, caretakers, clinicians, and other users associated with the stimulation systems.

As one illustrative benefit, a sensor-compliant stimulation strategy may be determined and used (as will be described in more detail below) to enable a stimulation system to monitor physiological conditions of a recipient without necessarily requiring additional sensors or hardware to be set up and without sacrificing or interfering with the performance of the stimulation system in any way that is noticeable by or detrimental to the recipient. As will be described in more detail below, one benefit of employing such a stimulation strategy is that different types of physiological conditions that are effectively monitored at different rates (e.g., including rates that vary widely by one or more orders of magnitude, etc.) may be scheduled for monitoring within the stimulation strategy in a predictable manner that allows these physiological conditions to be effectively and efficiently monitored without interfering with stimulation operations of the stimulation system in a way that would be perceivable or detrimental to the recipient of the stimulation system.

As another benefit, a stimulation system may be more power-efficient and effective as a result of being able to predictably control and plan for detecting and monitoring physiological conditions. This predictability allows systems described herein to power up and shut down certain measurement blocks of the system in an efficient and timely manner that optimizes power consumption (thereby saving battery power) and allows for cleaner signals to be captured and delivered.

Other illustrative benefits may relate to the relevant and real-time notifications that recipients and caretakers may receive to keep apprised of recipient physiological conditions. Moreover, various additional improvements to certain types of stimulation systems (e.g., improved beamforming and improved sound processing program selection in hearing systems, etc.) may be provided along with various beneficial new features that may be facilitated by physiological condition monitoring (e.g., alarms based on real-time sleep stages and/or sleep quality, warnings regarding episodes of pathologic conditions that may occur, etc.).

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein for monitoring and acting on a physiological condition of a stimulation system recipient may provide any of the benefits mentioned above, as well as various additional and/or alternative benefits that will be described and/or made apparent below.

FIG. 1 shows an illustrative stimulation system 100 configured to monitor and act on a physiological condition of a recipient. As will be described by way of several examples below, stimulation system 100 may be implemented in various different ways by hearing systems (e.g., cochlear implant systems, hearing aid systems, electroacoustic hearing systems, bimodal systems, etc.), neuromodulation systems, and/or other types of medical systems configured to apply stimulation to a recipient. While certain examples described herein may focus on a particular type of stimulation system, it will be understood that it may be possible for other types of stimulation systems to implement the principles being described (e.g., taking the place of the specific stimulation system implementations being described or operating in concert with those specific implementations).

As shown in FIG. 1, stimulation system 100 may include components such as, without limitation, a stimulation device 102 that is configured to apply stimulation 104 to a recipient, a sensing device 106 that is configured to detect a physiological condition of the recipient and a processing unit 108 that is communicatively coupled to stimulation device 102 and sensing device 106 by way of one or more communication links 110 (e.g., connected to stimulation device 102 by way of a communication link 110-1 and to sensing device 106 by way of a communication link 110-2 in this example).

Stimulation device 102 and stimulation 104 may be implemented in various different ways depending on what type of stimulation system implements stimulation system 100. For instance, as will be described in more detail below, stimulation device 102 may be implemented as a cochlear implant and associated electrode lead or as a hearing aid loudspeaker (also referred to as an acoustic receiver) for different hearing system examples. In these examples, stimulation 104 may include electrical and/or acoustic stimulation generated and applied (e.g., by way of the electrode lead or the loudspeaker, etc.) to facilitate the recipient's hearing. In other instances, stimulation device 102 may be implemented within other types of hearing systems (e.g., hearing systems configured to provide vibrotactile bone conduction to the middle or inner ear, etc.), neuromodulation systems (e.g., spinal cord stimulators, sacral stimulators, etc.), or other stimulation systems (e.g., cardiac pacemakers, etc.). In these examples, stimulation 104 may be provided as electrical, acoustic, mechanical (e.g., vibrotactile), electromagnetic (e.g., radio waves), optical (e.g., LED-based), and/or other suitable stimulation that interacts with a particular part of the body of the recipient. To this end, communication link 110-1 may represent any type of wireless or wired communication link as may serve a particular implementation of stimulation system 100.

Sensing device 106 may also be implemented in various ways depending on what types of physiological conditions a particular embodiment of stimulation system 100 is configured to monitor and/or use. Sensing device 106 may be implemented by any of various types of sensors or other such devices configured to monitor various functions of the recipient including heart-related functions, brain-related functions, and so forth. In some examples, a plurality of sensing devices (including sensing device 106) may be included within stimulation system 100 and used to monitor different types of physiological conditions.

Certain implementations of sensing device 106 may be used both to detect a physiological condition and to apply a certain type of stimulation. For instance, a sensing device 106 implemented as a cochlear implant electrode may be used to both stimulate an auditory nerve of the recipient as well as to detect an auditory potential produced by the brain of the recipient. In other instances, electrodes on the same cochlear implant electrode lead may be used for these purposes even if no single electrode performs both stimulation and sensing functions. In other implementations, sensing device 106 may be distinct from electrodes or other stimulation mechanisms used by stimulation device 102. For example, sensing device 106 may be implemented as a sensor placed near the heart or external to the head of the recipient while stimulation device 102 applies stimulation inside the cochlea of the recipient. Similar to communication link 110-1, communication link 110-2 may represent any type of wireless or wired communication link as may serve a particular implementation of stimulation system 100. Various implementations of stimulation device 102, stimulation 104, and sensing device 106 will be described in more detail below.

Processing unit 108 may be implemented by computing resources such as an embedded system of a cochlear implant or hearing aid sound processor, a computing device such as a mobile device (e.g., a smartphone, a tablet, a clinician device, etc.), or any other computing resources as may serve a particular implementation. Various implementations of processing unit 108 will be described below for different types of implementations of stimulation system 100.

As illustrated in FIG. 1, processing unit 108 may be included along with other components (e.g., stimulation device 102, sensing device 106, etc.) in certain implementations of stimulation systems 100. In other examples, however, an apparatus implementing processing unit 108 may serve as a full implementation of stimulation system 100 and may communicate with other devices (e.g., a stimulation device, a sensing device, etc.) that are separate from the apparatus.

As shown, processing unit 108 may include, without limitation, a memory 112 and a processor 114 selectively and communicatively coupled to one another. Memory 112 and processor 114 may each include or be implemented by computer hardware that is configured to store and/or execute computer instructions (e.g., software, firmware, etc.). Various other components of computer hardware and/or software not explicitly shown in FIG. 1 may also be included within processing unit 108. In some examples, memory 112 and processor 114 may be distributed between multiple devices as may serve a particular implementation.

Memory 112 may store and/or otherwise maintain executable data used by processor 114 to perform any of the functionality described herein. For example, memory 112 may store instructions 116 that may be executed by processor 114. Memory 112 may be implemented by one or more memory or storage devices, including any memory or storage devices described herein, that are configured to store data in a transitory or non-transitory manner. Instructions 116 may be executed by processor 114 to cause processing unit 108 to perform any of the functionality described herein. Instructions 116 may be implemented by any suitable application, software, firmware, script, code, and/or other executable data instance. Additionally, memory 112 may also maintain any other data accessed, managed, used, and/or transmitted by processor 114 in a particular implementation.

Processor 114 may be implemented by one or more computer processing devices, including general purpose processors (e.g., central processing units ("CPUs"), microprocessors, etc.), special purpose processors (e.g., application-specific integrated circuits ("ASICs"), field-programmable gate arrays ("FPGAs"), etc.), or the like. Using processor 114 (e.g., when processor 114 is directed to perform operations represented by instructions 116 stored in memory 112), processing unit 108 may perform functions associated with monitoring and acting on a physiological condition of a recipient as described herein and/or as may serve a particular implementation.

Figure 2:
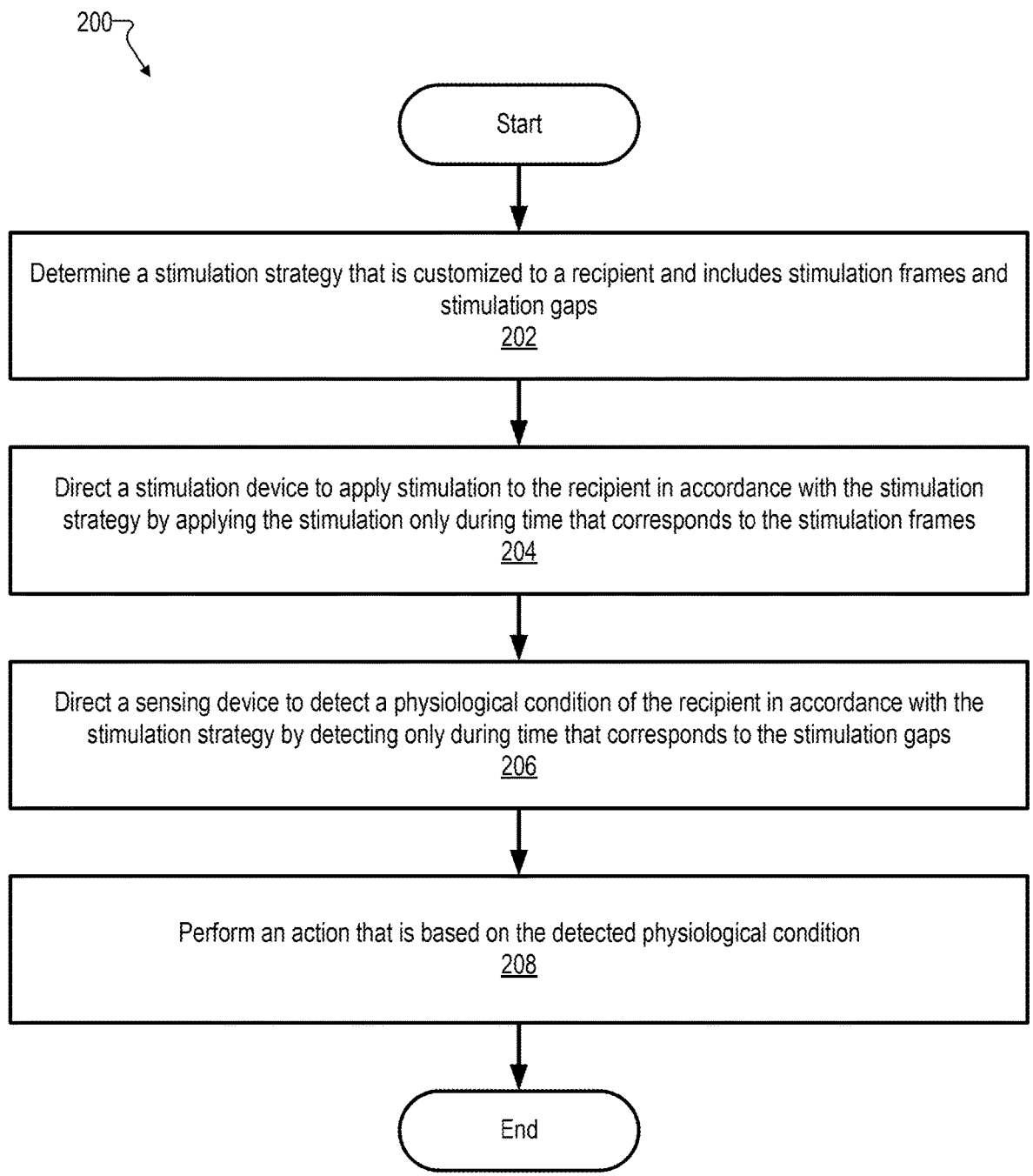
FIG. 2 shows an illustrative method for monitoring and acting on a physiological condition of a recipient.

As one example of functionality that processor 114 may perform, FIG. 2 shows an illustrative method 200 for monitoring and acting on a physiological condition of a stimulation system recipient in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 or described in relation to FIG. 2 may be performed concurrently (e.g., in parallel) with one another, rather than being performed sequentially as illustrated and/or described. One or more of the operations shown in FIG. 2 may be performed by a stimulation system such as system 100 and/or any implementation thereof. For instance, method 200 may be performed by a hearing system such as one of the cochlear implant systems, hearing aid systems, or other hearing systems described herein. As another example, method 200 may be performed by a neuromodulation system such as any of the neuromodulation systems described herein.

In some examples, the operations of FIG. 2 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Each of operations 202-208 of method 200 will now be described in more detail as the operations may be performed by stimulation system 100 (e.g., by processing unit 108), an implementation thereof, or another suitable stimulation system.

At operation 202, stimulation system 100 may determine a stimulation strategy that is customized to a recipient of stimulation system 100. For example, the stimulation strategy may include stimulation frames during which processing unit 108 may direct stimulation device 102 to apply stimulation 104 to the recipient (e.g., as described below in relation to operation 204), as well as stimulation gaps during which processing unit 108 may direct sensing device 106 to detect a physiological condition of the recipient (e.g., as described below in relation to operation 206).

The stimulation strategy determined at operation 202 may be customized to the recipient in any suitable way. For example, the customization of the stimulation strategy may allow for physiological condition monitoring to be performed concurrently with normal operation of stimulation system 100 in a way that the recipient does not notice (or is not adversely affected by) any change to the stimulation performance of stimulation system 100. The stimulation strategy may be customized in various ways, for instance, so as to minimize the impact to a particular recipient based on the recipient's unique sensitivity, hearing capability, preferences, and so forth.

As one example, stimulation system 100 may, as part of the determining of the stimulation strategy at operation 202, perform various functions to cater the stimulation strategy to the particular physiological condition and/or the particular recipient. For instance, stimulation system 100 may identify a type of physiological condition that is to be detected, and, based on the identified type of physiological condition, select a length of the stimulation frames and/or a length of the stimulation gaps. As used herein, a length of a stimulation frame or stimulation gap may refer to a period of time (e.g., a pulse width, a duration, etc.) during which the respective stimulation frames and/or stimulation gaps are performed or scheduled in the stimulation strategy. For example, since different types of physiological conditions may require different lengths or frequencies of gaps to be properly measured and/or monitored, these characteristics of the physiological conditions may be accounted for in the lengths of the stimulation frames and gaps, as well as in the scheduling of which gaps may be used to detect which physiological conditions, as will be described in more detail below.

Another way that stimulation system 100 may customize the stimulation strategy to the physiological condition and/or the recipient at operation 202 is by determining a temporal pattern for the stimulation gaps and the stimulation frames based on the identified type of physiological condition and/or based on a characteristic of the recipient. As will be described in more detail below, for example, the temporal pattern may relate to a schedule of when stimulation frames and stimulation gaps are to occur in the stimulation strategy. In certain cases, this schedule may also indicate which functions are to be performed in which stimulation gaps (e.g., which physiological conditions are to be measured when) in order to account for different frequencies and/or detection times that may be appropriate for measuring different types of physiological conditions and/or in order to perform functions unrelated to detecting physiological conditions of the recipient where useful for a particular implementation.

In some examples, the characteristic of the recipient used to form the basis for the temporal pattern determination may be a stimulation gap perception ability of the recipient. As used herein, a stimulation gap perception ability may refer to the ability that a particular recipient may have to perceive stimulation gaps when those gaps are added at higher frequencies and/or with longer durations within a particular stimulation strategy. For example, it may be the case that one particular recipient does not perceive stimulation gaps having a certain frequency or a certain duration while these gaps are perceived by a different recipient. In this example, these two recipients would be said to have different stimulation gap perception abilities and these abilities may be taken into account during the determination of respective stimulation strategies customized to these particular recipients.

In certain implementations, stimulation system 100 may determine a stimulation gap perception ability of a recipient by receiving, from the recipient, behavioral input representative of the stimulation gap perception ability of the recipient. For example, as stimulation gaps are increased (e.g., in frequency, duration, in both frequency and duration, or in another suitable way) during a perception test, the recipient may indicate behaviorally (e.g., verbally or by pressing a button, etc.) when he or she notices the gaps or somehow perceives that the stimulation quality is diminished. In contrast, in other implementations, stimulation system 100 may determine the stimulation gap perception ability of a recipient by automatically detecting the stimulation gap perception ability of the recipient without behavioral input received by the recipient. For example, this may be done by detecting brain waves of the recipient as perception tests are performed, as will be described in more detail below. In still other implementations, system 100 may customize the stimulation strategy using a hybrid approach that accounts both for behavioral input and automatically-detected brain wave patterns of the recipient to identify the most optimal lengths of stimulation gaps and/or to otherwise optimally customize the stimulation strategy that is to be used for a particular recipient.

At operation 204, stimulation system 100 may direct stimulation device 102 to apply stimulation 104 to the recipient in accordance with the stimulation strategy determined at operation 202. For example, stimulation system 100 may direct stimulation device 102 to apply stimulation 104 only during time that corresponds to the stimulation frames, and not during time that corresponds to the stimulation gaps. During the time that corresponds to the stimulation frames, the stimulation of the recipient at operation 204 may be performed in accordance with principles described herein that are particular to the type of stimulation system implemented in a given example. For example, cochlear implant system stimulation may involve applying electrical stimulation to cochlear tissue of the recipient by way of an electrode lead connected to a cochlear implant, while hearing aid stimulation may involve applying acoustic stimulation to an inner ear of the recipient by way of a loudspeaker of a hearing aid.

At operation 206, stimulation system 100 may direct sensing device 106 to detect the physiological condition of the recipient in accordance with the stimulation strategy determined at operation 202. For example, stimulation system 100 may direct sensing device 106 to perform the detecting only during time that corresponds to the stimulation gaps. The detecting of operation 206 may involve one-off or as-needed measurements of certain physiological conditions, and may involve continuous monitoring of other physiological conditions.

The one or more physiological conditions detected at operation 206 may be any suitable conditions or characteristics of the recipient as may relate to the overall physiology of the recipient (e.g., including average or real-time physiological conditions or characteristics). In some examples, a physiological condition may be associated with the health of the recipient, a sentiment (e.g., mood, emotions, etc.) of the recipient, a behavior of the recipient, or another suitable characteristic as described herein. More particularly, health conditions of the recipient that may be detected and/or monitored may include, for example, heart rate (e.g., pulse rate), heart rate variability, brain wave patterns, sleep patterns, and various other conditions and characteristics associated with the recipient's health as may serve a particular implementation. Sentiment conditions of the recipient that may be detected and/or monitored may include any of various psychophysiological conditions (e.g., subjective feelings that manifest with physiological symptoms) such as, for example, stress, sleepiness, calmness, attentiveness, and/or various other aspects of sentiment that may be detectable based on outward physiological characteristics (e.g., brain waves, heart rate, etc.). Behavioral conditions of the recipient that may be detected and/or monitored may include actions that the recipient takes such as looking in one direction instead of another (e.g., looking left instead of right, etc.), focusing his or her attention, sleeping, exercising, and/or any other behavior that may be detectable based on the outward physiological characteristics.

The detecting of physiological conditions at operation 206 may be performed in any suitable manner and/or using any suitable sensors, tools, tests, techniques, or the like, as may serve a particular implementation. For instance, sensing device 106 may use or be implemented by one or more of the following, or another suitable sensor or tool, to detect a physiological condition of the recipient: an electrocardiogram ("EKG") sensor for detecting a heart rate variability of the recipient, an electroencephalogram ("EEG") sensor for detecting a brain wave pattern of the recipient (e.g., an evoked or non-evoked potential, an auditory potential, a cortical potential, etc.), an electromyogram ("EMG") sensor for detecting a muscle tissue function of the recipient, an electrooculogram ("EOG") sensor for performing eye monitoring for the recipient, a photoplethysmogram ("PPG") sensor for detecting blood volume changes in the recipient, a skin contact sensor for performing electrodiagnostic monitoring of the recipient, or an orientational sensor for detecting an orientation of the recipient.

These sensors, the respective tests they perform, and the physiological conditions they are configured to monitor will be understood to be examples only. In other implementations, various other types of sensing devices (e.g., sensors included within stimulation system 100 like sensing device 106, sensors external to stimulation system 100, etc.) may additionally or alternatively be employed as may serve a particular embodiment. For instance, as will be described in more detail below, in the case of a cochlear implant system implementation of stimulation system 100, the detecting of the physiological condition at operation 206 may be performed by way of one or more electrodes of an array of electrodes on an electrode lead included within the cochlear implant system. In other instances, sensors such as pressure sensors, spectroscopy sensors, optical sensors, chemical sensors, or other suitable sensors may be employed.

In some examples described herein, raw data detected by way of a test such as an EKG or EEG test may be post-processed to determine the physiological condition (rather than the physiological condition being represented by the raw data itself). For example, as will be described in more detail below, data captured during an EEG test may be analyzed to determine that the recipient is blinking at a certain rate, looking in a particular direction, or performing another such behavior. As another example, an EKG test may be analyzed to determine that the recipient is feeling stressed or calm based on the heart rate variability and/or other detected conditions. Heart rate variability (i.e., the skew or time variation from beat to beat of the heart) may be indicative or suggestive of human health or sentiment (e.g., stress levels, etc.) because the variation between heart beats generally increases with increased stress. Accordingly, by measuring heart rate variability, a general stress level or a relative stress level of a person may be determined based on the heart rate variability.

Processing unit 108 may measure, and continuously monitor over time, the heart rate variability of the recipient using a sensor (e.g., an EKG sensor) built into or communicatively coupled with stimulation system 100. Based on the monitored heart rate variability, processing unit 108 may determine the heart rate of the recipient, and the detected physiological condition may correspond to a heart rate variability condition or another condition indicated by the heart rate itself. The heart rate variability condition may also have an established correlation with a particular sentiment of the recipient (e.g., the level of stress or calm the recipient is feeling, etc.) such that stimulation system 100 may determine the sentiment that the recipient is feeling based on the heart rate variability condition in certain examples.

As another example of a physiological condition that may be monitored along with or instead of heart rate and heart rate variability, EEG monitoring may be used to detect and analyze alpha waves or other non-evoked potentials emitted by the brain and analyzable as different frequency peaks in the EEG wave to determine what the alpha waves suggest about the health and/or sentiment of the recipient. In some examples, stimulation system 100 may consider EEG alpha wave data together with other data described herein to identify various physiological conditions of the recipient, as will be described in more detail below.

As additional examples of physiological conditions that may be monitored, operation 206 may involve monitoring a state of the recipient with respect to a situation the recipient is experiencing (e.g., sleep, surgery, etc.), with respect to a pathologic condition the recipient suffers from (e.g., epilepsy, tinnitus, etc.), or the like. For example, stimulation system 100 may monitor an anesthesia state and/or a pain level of the recipient during surgery. As another example, stimulation system 100 may monitor a state of the recipient in relation to epileptic characteristics such as epileptic seizures or other involuntary behaviors to which the recipient may be prone. This type of monitoring may be performed in any suitable way, such as based on brain waves detected during EEG testing.

As mentioned above, in certain examples, stimulation system 100 may be configured to monitor more than one type of physiological condition at once. For example, along with sensing device 106, stimulation system 100 may include an additional sensing device configured to detect an additional physiological condition of the recipient (e.g., a physiological condition of a different physiological condition type than the physiological condition). In this example, the directing of sensing device 106 to detect the physiological condition may include directing sensing device 106 to detect the physiological condition only during time that corresponds to a first subset of the stimulation gaps, and processing unit 108 may be further configured to direct the additional sensing device to detect the additional physiological condition only during time that corresponds to a second subset of the stimulation gaps (e.g., a subset that is distinct from the first subset of the stimulation gaps).

In this way, a plurality of physiological conditions may be monitored, each at their own respective frequency as may best serve that type of physiological condition, by a plurality of different sensing devices. For example, the stimulation strategy determined at operation 102 may schedule stimulation gaps at a 1 kHz rate to be used for monitoring a first type of physiological condition by a first sensing device, schedule stimulation gaps at a 100 Hz rate to be used for monitoring a second type of physiological condition by a second sensing device, and so forth for any number of physiological conditions and sensing devices and for any frequency as may be appropriate for monitoring them. Because the stimulation strategy is carefully determined and customized to the recipient, the stimulation gaps may be partitioned out in these ways to allow monitoring of various types of physiological conditions at various rates without compromising the quality of the stimulation being provided to the recipient.

At operation 208, stimulation system 100 may perform an action based on one or more physiological conditions that have been detected at operation 206. This action may be any suitable action as may correspond to the detected physiological condition in any suitable way. For instance, the action performed at operation 208 may include adjusting a stimulation parameter of the stimulation system, providing various types of notifications to the recipient or another user (e.g., a caretaker of the recipient), providing stimulation to mitigate an epileptic episode that has been detected to be occurring or imminent, and/or any of various other actions described herein or as may serve a particular implementation. For hearing system examples in particular, other examples of actions that may be performed could include performing beamforming operations to help the recipient narrow in on a certain speech source, switching to a different sound processing program than is currently in use (e.g., a comfort program, etc.), altering a noise reduction parameter, or the like.

FIGS. 3A-3B show illustrative implementations 300 of stimulation system 100. Specifically, FIG. 3A shows a hearing system 300-A and FIG. 3B shows a neuromodulation system 300-B. While implementations 300 represent two categories of stimulation system implementations that may employ systems and methods for monitoring and acting on physiological condition of recipients, it will be understood that these are not the only types of stimulation systems that may be implemented in accordance with principles described herein. Additionally, as will be further described below, it will be understood that different types of hearing systems may implement hearing system 300-A and that different types of neuromodulation systems may implement neuromodulation system 300-B.

Hearing system 300-A in FIG. 3A is shown to include a processing unit 302-A that is communicatively coupled to a stimulation device 304-A. Processing unit 302-A may implement processing unit 108 of stimulation system 100, while stimulation device 304-A may serve as an implementation of stimulation device 102. As shown, stimulation device 304-A may be configured to apply either or both of electrical stimulation 306-A and acoustic stimulation 306-A2 to serve as an implementation of stimulation 104. Each of a plurality of N sensors 308-A (e.g., sensors 308-A through 308-AN) may implement a sensing device such as sensing device 106 of stimulation system 100. As described above, each sensor 308-A may be configured to detect a different type of physiological condition at a different rate that is suitable for effectively detecting the physiological condition and that accounts for sensitivities, preferences, and/or other characteristics of the recipient. It will be understood that, as used herein, "N" may be used as a placeholder value 1 or greater to generically relate the number of various different types of items described herein. As such, an N used to describe the number of one type of item herein may be different than an N used to describe the number of another item herein.

Processing unit 302-A may be implemented by one or more devices configured to interface with stimulation device 304-A and sensors 308-A. For example, processing unit 302-A may be implemented as a sound processor of a cochlear implant system or a hearing aid system configured to receive and present an audio signal in real time. For instance, audio signals including speech and/or other types of sound may be detected from the environment of the recipient by a microphone 310, or may be otherwise obtained (e.g., provided by another system such as a music player, a streamer device, a telecoil, etc.). The sound processor implementing processing unit 302-A of hearing system 300-A may be implemented by any suitable device that may be worn or carried by the recipient. For example, cochlear implant system implementations of hearing system 300-A may use a sound processor implemented by a behind-the-ear ("BTE") unit configured to be worn behind and/or on top of an ear of the recipient, by an off-the-ear unit (also referred to as a body worn device) configured to be worn or carried by the recipient away from the ear, or the like. Hearing aid system implementations of hearing system 300-A may integrate the sound processor into a small form factor that is worn inside the concha of the ear.

Microphone 310 may be implemented in any suitable manner. For example, microphone 310 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to the sound processor implementing processing unit 302-A. Additionally or alternatively, microphone 204 may be implemented by one or more microphones in or on a headpiece of a cochlear implant system, one or more microphones integrated into or onto a housing of a hearing aid in a hearing aid system, one or more beam-forming microphones, and/or any other suitable microphone or set of microphones as may serve a particular implementation.

Hearing system 300-A may be implemented as various types of hearing systems depending on the needs of the recipient at each of his or her ears. For example, if a particular recipient lacks any hearing ability at both ears, a bilateral cochlear implant system may be used to electrically stimulate the auditory nerve at each cochlea of the recipient using electrical stimulation 306-A1. As another example, the recipient may suffer only partial hearing loss in each ear (e.g., difficulty in perceiving sound only at certain frequencies) such that a hearing aid system that provides acoustic stimulation 306-A2 is most appropriate to facilitate the hearing of the recipient. In still other examples, certain cochlear implant recipients may retain partial hearing in one or both ears, such as an ability to hear only certain frequencies. Such recipients may benefit from a hybrid approach of an electroacoustic hearing system that may provide both the electrical stimulation 306-A1 of a cochlear implant system (e.g., for certain frequencies) and the acoustic stimulation 306-A2 of a hearing aid system (e.g., for other frequencies). Certain implementations of hearing system 300-A may also include bimodal hearing systems that employ one type of hearing system (e.g., a hearing aid system providing acoustic stimulation 306-A2) for one ear and another type of hearing system (e.g., a cochlear implant system providing electrical stimulation 306-A1 or an electroacoustic hearing system providing both electrical and acoustic stimulation 306-A1 and 306-A2) for the other ear. Certain example implementations of hearing system 300-A will be described in more detail below.

Neuromodulation system 300-B in FIG. 3B may include a processing unit and a stimulation device configured to modulate neurological signals produced by the recipient to treat a medical condition from which the recipient suffers by applying electrical stimulation to the recipient. For example, neuromodulation system 300-B may be implemented by a non-hearing stimulation system such as a spinal cord stimulator, a sacral stimulator, a spinal drug delivery system, a brain stimulator, a peripheral nerve stimulator, or the like. As shown, neuromodulation system 300-B may include a processing unit 302-B that is communicatively coupled to a stimulation device 304-B. In this example, processing unit 302-B may implement processing unit 108 of stimulation system 100, while stimulation device 304-B may serve as an implementation of stimulation device 102. As shown, stimulation device 304-B may be configured to apply electrical stimulation 306-B to serve as an implementation of stimulation 104. Each of a plurality of N sensors 308-B (e.g., sensors 308-B1 through 308-BN) may implement a sensing device such as sensing device 106 of stimulation system 100.

Processing unit 302-B may be implemented by one or more devices configured to interface with stimulation device 304-B to direct stimulation device 304-B to properly apply neuromodulation stimulation aimed at relieving pain of the recipient, treating a condition of the recipient (e.g., epilepsy, Parkinson's disease, incontinence, angina, peripheral vascular disease, etc.), or otherwise improving the experience of the recipient. Processing unit 302-B may also direct sensors 308-B to monitor any of the physiological conditions of the recipient described herein. As described above, each sensor 308-B may be configured to detect a different type of physiological condition at a different rate that is suitable for effectively detecting the physiological condition and that accounts for sensitivities, preferences, and/or other characteristics of the recipient.

As one particular example of how a neuromodulation system such as neuromodulation system 300-B may assist and serve a recipient, the medical condition that electrical stimulation 306-B is applied to treat may be an epileptic condition. In this example, processing unit 302-B may be configured to detect an occurrence of one or more epileptic events experienced by the recipient. The determining of the stimulation strategy and the directing of stimulation device 304-B to apply electrical stimulation 306-B to the recipient may then be performed based on the detected occurrence of the one or more epileptic events experienced by the recipient.

FIGS. 4A-4D show illustrative implementations of hearing system 300-A. More particularly, FIG. 4A shows a cochlear implant system 400-A that itself may be implemented in different ways illustrated by cochlear implant system 400-B of FIG. 4B and cochlear implant system 400-C of FIG. 4C, while FIG. 4D shows a hearing aid system 400-D.

Cochlear implant systems 400-A through 400-C each include an electrode lead having an array of electrodes, as well as a cochlear implant that, when implanted within the recipient together with the electrode lead, may be configured to apply electrical stimulation to the recipient by way of the array of electrodes. Using these components, each cochlear implant system implementation may be configured to perform method 200 by 1) determining a stimulation strategy that is customized to the recipient and includes stimulation frames and stimulation gaps, 2) directing the cochlear implant to apply electrical stimulation to the recipient in accordance with the stimulation strategy by applying the stimulation only during time that corresponds to the stimulation frames, 3) detecting a physiological condition of the recipient during time that corresponds to the stimulation gaps, and 4) performing an action based on the detected physiological condition.

Similarly, hearing aid system 400-D includes a hearing aid configured to be worn by the recipient on an ear of the recipient and a loudspeaker associated with the hearing aid and configured, when the hearing aid is worn by the recipient, to apply the acoustic stimulation to the recipient. Using these components, hearing aid system 400-D may be configured to perform method 200 by 1) determining a stimulation strategy that is customized to the recipient and includes stimulation frames and stimulation gaps, 2) directing the loudspeaker to apply acoustic stimulation to the recipient in accordance with the stimulation strategy by applying the stimulation only during time that corresponds to the stimulation frames, 3) detecting a physiological condition of the recipient during time that corresponds to the stimulation gaps, and 4) performing an action based on the detected physiological condition.

Each of hearing systems 400 (cochlear implant systems 400-A through 400-C and hearing aid system 400-D) will now be described in more detail.

As shown in FIG. 4A, cochlear implant system 400-A includes a cochlear implant 402, an electrode lead 404 physically coupled to cochlear implant 402 and having an array of electrodes 406, and a processing unit 408 configured to be communicatively coupled to cochlear implant 402 by way of a communication link 410. Cochlear implant 402, electrode lead 404 and electrodes 402 may collectively implement stimulation device 304-A of hearing system 300-A and/or stimulation device 102 of stimulation system 100. Processing unit 408 may implement processing unit 302-A of hearing system 300-A and/or processing unit 108 of stimulation system 100. As will be described in more detail below, one or more of sensors 308-A may be implemented by one or more electrodes 406 and the mechanisms by which processing unit 408 uses these electrodes to detect physiological conditions of the recipient (e.g., electrode lead 404, cochlear implant 402, etc.). Other sensors 308-A are not explicitly shown for the implementations of cochlear implant system 400-A in FIGS. 4A-4C but will be understood to connect to processing unit 408 in any suitable manner.

The cochlear implant system 400-A shown in FIG. 4A is unilateral (i.e., associated with only one ear of the recipient). Alternatively, as mentioned above, a bilateral configuration of cochlear implant system 400-A may include separate cochlear implants and electrode leads for each ear of the recipient. In the bilateral configuration, processing unit 408 may be implemented by a single processing unit configured to interface with both cochlear implants or by two separate processing units each configured to interface with a different one of the cochlear implants.

Cochlear implant 402 may be implemented by any suitable type of implantable stimulator. For example, cochlear implant 402 may be implemented by an implantable cochlear stimulator. Additionally or alternatively, cochlear implant 402 may be implemented by a brainstem implant and/or any other type of device that may be implanted within the recipient and configured to apply electrical stimulation to one or more stimulation sites located along an auditory pathway of the recipient.

In some examples, cochlear implant 402 may be configured to generate electrical stimulation representative of an audio signal processed by processing unit 408 in accordance with one or more stimulation parameters transmitted to cochlear implant 402 by processing unit 408. Cochlear implant 402 may be further configured to apply the electrical stimulation to one or more stimulation sites (e.g., one or more intracochlear locations) within the recipient by way of one or more electrodes 406 on electrode lead 404. In some examples, cochlear implant 402 may include a plurality of independent current sources each associated with a channel defined by one or more of electrodes 406. In this manner, different stimulation current levels may be applied to multiple stimulation sites simultaneously by way of multiple electrodes 406.

Cochlear implant 402 may additionally or alternatively be configured to generate, store, and/or transmit data. For example, cochlear implant may 402 use one or more electrodes 406 to record one or more signals (e.g., one or more voltages, impedances, evoked responses within the recipient, and/or other measurements) and transmit, by way of communication link 410, data representative of the one or more signals to processing unit 408. In some examples, this data is referred to as back telemetry data.

Electrode lead 404 may be implemented in any suitable manner. For example, a distal portion of electrode lead 404 may be pre-curved such that electrode lead 404 conforms with the helical shape of the cochlea after being implanted. Electrode lead 404 may alternatively be naturally straight or of any other suitable configuration.

In some examples, electrode lead 404 includes a plurality of wires (e.g., within an outer sheath) that conductively couple electrodes 406 to one or more current sources within cochlear implant 402. For example, if there are N electrodes 406 on electrode lead 404 and N current sources within cochlear implant 402, there may be N separate wires within electrode lead 404 that are configured to conductively connect each electrode 406 to a different one of the N current sources.

Electrodes 406 are located on at least a distal portion of electrode lead 404. In this configuration, after the distal portion of electrode lead 404 is inserted into the cochlea, electrical stimulation may be applied by way of one or more of electrodes 406 to one or more intracochlear locations. One or more other electrodes (e.g., including a ground electrode, not explicitly shown) may also be disposed on other parts of electrode lead 404 (e.g., on a proximal portion of electrode lead 404) to, for example, provide a current return path for stimulation current applied by electrodes 406 and to remain external to the cochlea after the distal portion of electrode lead 404 is inserted into the cochlea. Additionally or alternatively, a housing of cochlear implant 402 may serve as a ground for stimulation current applied by electrodes 406.

Processing unit 408 may be configured to interface with (e.g., control and/or receive data from) cochlear implant 402. For example, processing unit 408 may transmit commands (e.g., stimulation parameters and/or other types of operating parameters in the form of data words included in a forward telemetry sequence) to cochlear implant 402 by way of communication link 410. Processing unit 408 may additionally or alternatively provide operating power to cochlear implant 402 by transmitting one or more power signals to cochlear implant 402 by way of communication link 410. Processing unit 408 may additionally or alternatively receive data (e.g., in a backward telemetry sequence) from cochlear implant 402 by way of communication link 410. Communication link 410 may be implemented by any suitable number of wired and/or wireless bidirectional and/or unidirectional links.

As shown, processing unit 408 includes a memory 412 and a processor 414 configured to be selectively and communicatively coupled to one another. In some examples, memory 412 and processor 414 may be distributed between multiple devices and/or multiple locations as may serve a particular implementation.

Memory 412 may be implemented by any suitable non-transitory computer-readable (e.g., processor-readable) medium such as any combination of non-volatile storage media and/or volatile storage media. Examples of non-volatile storage media may include read-only memory, flash memory, a solid-state drive, a magnetic storage device (e.g., a hard drive), ferroelectric random-access memory ("RAM"), an optical disc, and so forth. Examples of volatile storage media may include RAM (e.g., dynamic RAM) or other types of volatile memory.

Memory 412 may maintain (e.g., store) executable data used by processor 414 to perform one or more of the operations described herein. For example, memory 412 may store instructions 416 that may be executed by processor 414 to perform any of the operations described herein. Instructions 416 may be implemented by any suitable application, program (e.g., sound processing program), software, script, code, and/or other executable data instance. Memory 412 may also maintain any data received, generated, managed, used, and/or transmitted by processor 414.

Processor 414 may be configured to perform (e.g., execute instructions 416 stored in memory 412 to perform) various operations with respect to cochlear implant 402. For instance, processor 414 may perform any of the operations described herein as being performed by processing unit 408, including directing operations performed by cochlear implant 402. As one illustrative operation, processor 414 may receive an audio signal (e.g., by way of a microphone communicatively coupled to processing unit 408, a wireless interface (e.g., a Bluetooth interface), and/or a wired interface (e.g., an auxiliary input port)). Processor 414 may process the audio signal in accordance with a sound processing program (e.g., a sound processing program stored in memory 412) to generate appropriate stimulation parameters. Processor 414 may then transmit the stimulation parameters to cochlear implant 402 to direct cochlear implant 402 to apply electrical stimulation representative of the audio signal to the recipient.

In some implementations, processor 414 may also be configured to apply acoustic stimulation to the recipient. For example, cochlear implant system 400-A may be implemented as an electroacoustic hearing system that includes, together with the electrode lead for applying electrical stimulation to the recipient, a loudspeaker (also referred to as an acoustic receiver) that is optionally coupled to processing unit 408 for delivering acoustic stimulation to the recipient. The acoustic stimulation may be representative of an audio signal (e.g., an amplified version of the audio signal), and may be configured to produce sound at frequencies that the recipient retains an ability to hear and, in certain examples, to produce acoustic stimulation that may elicit an evoked response within the recipient.

Processor 414 may be additionally or alternatively configured to receive and process data generated by cochlear implant 402. For example, processor 414 may receive data representative of a signal recorded by cochlear implant 402 using one or more electrodes 406 and, based on the data, adjust one or more operating parameters of processing unit 408. Additionally or alternatively, processor 414 may use the data to perform one or more diagnostic operations with respect to cochlear implant 402 and/or the recipient.

Other operations may be performed by processor 414 as may serve a particular implementation. In the description provided herein, any references to operations performed by processing unit 408 and/or any implementation thereof may be understood to be performed by processor 414 based on instructions 416 stored in memory 412.

As mentioned above, certain sensors 308-A or sensing devices 106 may be implemented within cochlear implant system 400-A by one or more electrodes 406 of electrode lead 404, while other sensors 308-A and/or sensing device 106 implementations may be implemented by other types of sensing devices described herein (not explicitly shown in FIG. 4A). In examples in which the detecting of the physiological condition is performed by way of one or more electrodes 406 of the array of electrodes on electrode lead 404, the stimulation strategy may be determined accordingly. For example, the stimulation strategy may indicate that processing unit 408 is to direct cochlear implant 402 to apply electrical stimulation (e.g., electrical stimulation 306-A1) to the recipient by way of a first subset of electrodes 406 of the array of electrodes 406 of electrode lead 404. The stimulation strategy may further indicate that processing unit 408 is to detect the physiological condition of the recipient by way of a second subset of electrodes 406 of the array of electrodes 406, where the second subset of electrodes 406 is distinct and non-overlapping with the first subset of electrodes 406 (i.e., no electrode is common to both subsets). In other words, in these examples, different electrodes 406 may be used for applying the stimulation and for detecting physiological conditions such as auditory potentials.

In other examples, the first and second subset of electrodes 406 may be identical or distinct but overlapping (i.e., at least one electrode may be common to both subsets while at least one electrode is not common to both subsets). In other words, in these examples, cochlear implant system 400-A may employ at least one of the same electrodes to perform both stimulation and physiological condition monitoring functions at different times (e.g., during the stimulation frames and during the stimulation gaps defined in the stimulation strategy).

Examples in which particular electrodes 406 are selected for the second subset (i.e., for monitoring physiological conditions) may involve electrodes deemed, for various reasons, to be suboptimal (or, in certain examples, completely unsuitable) for stimulating the cochlea in normal operation. For instance, due to placement of the electrodes, in combination with unique characteristics associated with a particular cochlea of a particular recipient, certain electrodes may evoke a strange percept, may stimulate the facial nerve, may be shown in a CT scan to be placed suboptimally, or may otherwise be relatively poorly suited for normal cochlear stimulation as compared to the remainder of the electrodes. Processing unit 408 may identify such electrodes and rely exclusively (or at least more heavily) on these electrodes for monitoring physiological conditions in the ways described herein.

In certain implementations employing the designated first and second subsets of electrodes 406 for stimulation and physiological condition monitoring, processing unit 408 may perform dynamic assignment of which electrodes 406 are to be used for stimulation and for physiological condition monitoring based on the particular use case. For example, the stimulation strategy may be configured such that processing unit 408 allocates more electrodes 406 to the first subset in use cases where only sparse physiological condition monitoring is needed (e.g., use cases where the signal of interest is slow brain waves, use cases where dense stimulation is required for suitable operation, use cases where sparse recording is all that is needed for suitable operation, etc.). Conversely, when more continuous monitoring is needed, the stimulation strategy may be configured such that processing unit 408 allocates fewer electrodes 406 to the first subset and/or more electrodes 406 to the second subset. In certain examples, the stimulation strategy may designate a few electrodes 406 as dedicated monitoring electrodes due to their cochlear placement, impedance level, recovery characteristics, and/or other characteristics. To avoid impact on performance for the recipient, SPAN stimulation may be used on adjacent electrodes 406. Alternatively, stimulation electrodes and monitoring electrodes (also referred to as "recording electrodes") may be selected based on performance characteristics or preferences of the recipient.

Processing unit 408 may be implemented by one or more devices configured to interface with cochlear implant 402. To illustrate, FIG. 4B shows an illustrative implementation of cochlear implant system 400-A referred to as cochlear implant system 400-B. In this implementation, processing unit 408 is implemented by a sound processor 418 configured to be located external to the recipient. Sound processor 418 may implement any of the sound processors described above in relation to processing unit 302-A of hearing system 300-A, and, as such, may be communicatively coupled to a microphone 420 implementing microphone 310.

Additionally, as shown, sound processor 418 may be communicatively coupled to a headpiece 422 that is configured to be located external to the recipient along with sound processor 418 in this example. Headpiece 422 may be selectively and communicatively coupled to sound processor 418 by way of a communication link implemented by a cable or any other suitable wired or wireless communication link as may serve a particular implementation. Headpiece 422 may include an external antenna (e.g., a coil and/or one or more wireless communication components) configured to facilitate selective wireless coupling of sound processor 418 to cochlear implant 402. Headpiece 422 may additionally or alternatively be used to selectively and wirelessly couple any other external device to cochlear implant 402. To this end, headpiece 422 may be configured to be affixed to the recipient's head and positioned such that the external antenna housed within headpiece 422 is communicatively coupled (e.g., by way of an inductive link) to a corresponding implantable antenna such as an implanted coil (and/or one or more other wireless communication components) associated with cochlear implant 402. In this manner, stimulation parameters and/or power signals may be wirelessly and transcutaneously transmitted between sound processor 418 and cochlear implant 402 by way of a wireless and transcutaneous implementation of communication link 410.

In cochlear implant system 400-B, sound processor 418 may receive an audio signal detected by microphone 420 by receiving a signal (e.g., an electrical signal) representative of the audio signal from microphone 420. Sound processor 418 may additionally or alternatively receive the audio signal by way of any other suitable interface as described herein. Sound processor 418 may process the audio signal in any of the ways described herein and transmit, by way of headpiece 422, stimulation parameters to cochlear implant 402 to direct cochlear implant 402 to apply electrical stimulation representative of the audio signal to the recipient.

In an alternative configuration, sound processor 418 may be implanted within the recipient instead of being located external to the recipient. In this alternative configuration, which may be referred to as a fully implantable configuration of cochlear implant system 400-B, sound processor 418 and cochlear implant 402 may be combined into a single device or implemented as separate devices configured to communicate one with another by way of a wired and/or wireless communication link. In a fully implantable implementation of cochlear implant system 400-B, headpiece 422 may not be included and microphone 420 may be implemented by one or more microphones implanted within the recipient, located within an ear canal of the recipient, and/or located external to the recipient.

FIG. 4C shows an illustrative implementation of cochlear implant system 400-A referred to as cochlear implant system 400-C. In this implementation, processing unit 408 is implemented by a combination of sound processor 418 and a computing device 424 configured to communicatively couple to sound processor 418 by way of a suitable wired or wireless communication link.

Computing device 424 may be implemented by any suitable combination of hardware and software. To illustrate, computing device 424 may be implemented by a mobile device (e.g., a mobile phone, a laptop, a tablet computer, etc.), a desktop computer, a clinical tool configured to facilitate fitting the cochlear implant system to the recipient, and/or any other suitable computing device as may serve a particular implementation. As an example, computing device 424 may be implemented by a mobile device configured to execute an application (e.g., a "mobile app") that may be used by a user (e.g., the recipient, a clinician, and/or any other user). In some instances, such applications may be configured to control one or more settings of sound processor 418 and/or cochlear implant 402 and/or to perform one or more operations (e.g., diagnostic operations, fitting operations, etc.) with respect to data generated by sound processor 418 and/or cochlear implant 402.

In some examples, computing device 424 may be configured to control an operation of cochlear implant 402 by transmitting one or more commands to cochlear implant 402 by way of sound processor 418. Likewise, computing device 424 may be configured to receive data generated by cochlear implant 402 by way of sound processor 418. Alternatively, computing device 424 may interface with (e.g., control and/or receive data from) cochlear implant 402 directly by way of a wireless communication link between computing device 424 and cochlear implant 402. In some implementations in which computing device 424 interfaces directly with cochlear implant 402, sound processor 418 may or may not be included in cochlear implant system 400-C.

Computing device 424 is shown as having an integrated display 426. Display 426 may be implemented by a display screen or touchscreen, for example, and may be configured to display content generated by computing device 424. Additionally or alternatively, computing device 424 may be communicatively coupled to an external display device (not shown) configured to display the content generated by computing device 424.

In some examples, computing device 424 represents a fitting device configured to be selectively used (e.g., by a clinician) to fit sound processor 418 and/or cochlear implant 402 to the recipient. In these examples, computing device 424 may be configured to execute a fitting program configured to set one or more operating parameters of sound processor 418 and/or cochlear implant 402 to values that are optimized for the recipient. As such, in these examples, computing device 424 may not be considered to be part of cochlear implant system 400-C. Instead, computing device 424 may be considered to be separate from cochlear implant system 400-C such that computing device 424 may be selectively coupled to cochlear implant system 400-C when it is desired to fit sound processor 418 and/or cochlear implant 402 to the recipient.

In contrast to cochlear implant systems such as cochlear implant system 400-A and/or implementations thereof (e.g., cochlear implant systems 400-B and 400-C), hearing aid systems might not be implanted within the patient and might not include an electrode lead for directly applying electrical stimulation to the recipient. Instead, hearing aid systems leverage functional hearing that the recipient retains and apply acoustic stimulation in a manner that helps improve the hearing of the recipient (e.g., by accentuating frequencies that are difficult for the recipient to hear, etc.).

To illustrate, FIG. 4D shows hearing aid system 400-D, which includes a hearing aid 428 and a loudspeaker 432 communicatively coupled to hearing aid 428. Hearing aid 428 may be understood to implement processing unit 302-A of hearing system 300-A and/or processing unit 108 of stimulation system 100. Loudspeaker 432 may implement stimulation device 304-A of hearing system 300-A and/or stimulation device 102 of stimulation system 100. Sensing devices implementing sensors 308-A and/or sensing device 106 are not explicitly shown for hearing aid system 400-D but will be understood to connect to hearing aid 428 in any suitable manner. For example, an illustrative sensing device may be implemented by at least one sensor that is worn on the ear of the recipient and is sensitive to interference from the stimulation device (i.e., loudspeaker 432) and/or the processing unit (i.e., hearing aid 428). As such, the directing of this sensing device to detect the physiological condition only during the time that corresponds to the stimulation gaps may enable the sensing device to avoid the interference while performing the detecting of the physiological condition. For instance, it may be desirable to detect data from an orientational sensor (e.g., an accelerometer, a gyroscope, etc.), a skin contact sensor, a PPG sensor, or other such sensors while the acoustic stimulation is temporarily halted during preconfigured stimulation gaps planned for in the stimulation strategy.

Figure 5:
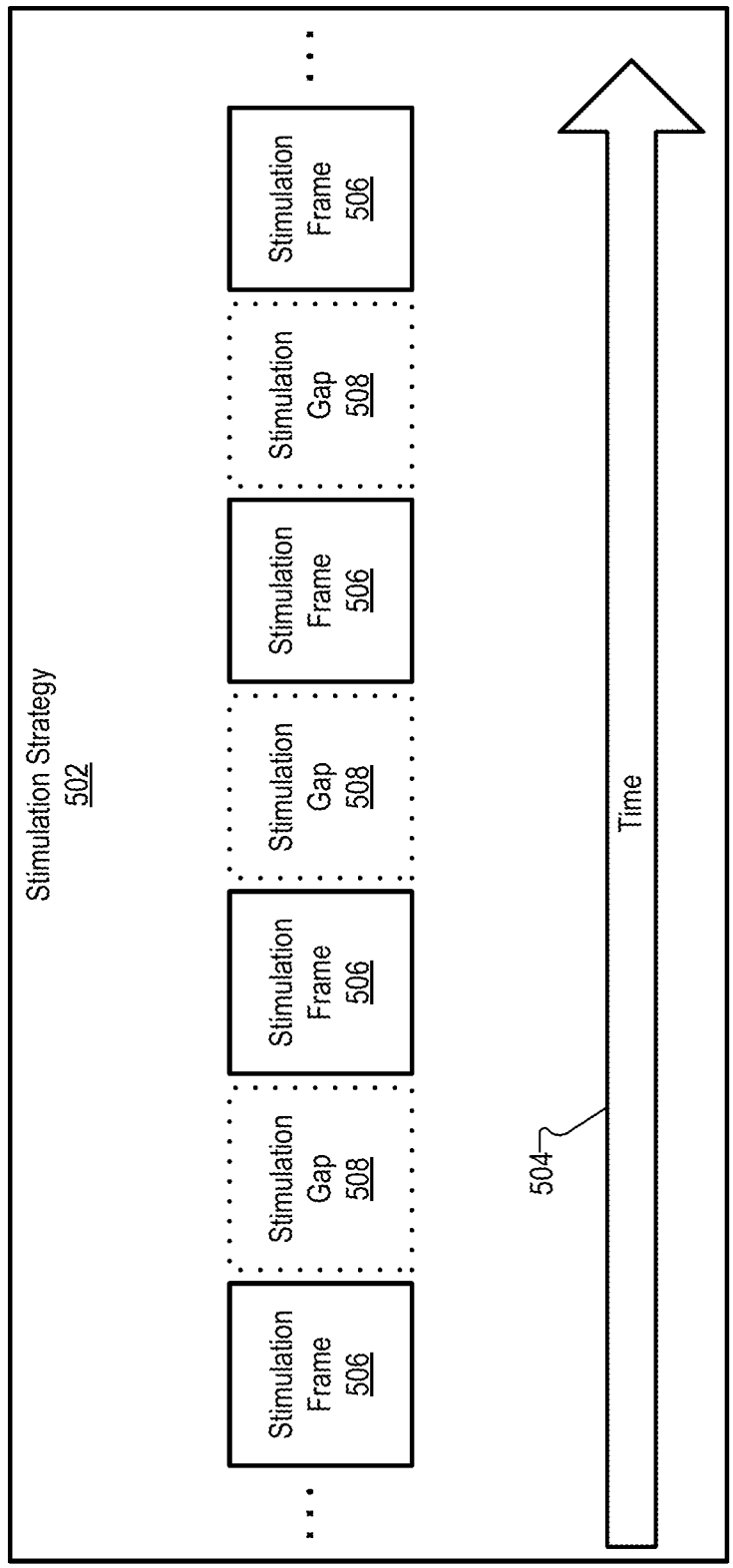
FIG. 5 shows an illustrative stimulation strategy for monitoring a physiological condition of a stimulation system recipient.

FIG. 5 shows an illustrative stimulation strategy 502 for monitoring a physiological condition of a hearing system recipient such as a recipient of any implementation of stimulation system 100 that has been described or that may serve a particular implementation. As described above in relation to operation 202, processing unit 108 may determine a stimulation strategy that is customized to the recipient and includes stimulation frames and stimulation gaps. Stimulation strategy 502 illustrates such a stimulation strategy. As shown, stimulation strategy 502 is defined with respect to a timeline 504 and includes a plurality of stimulation frames 506 separated by a plurality of stimulation gaps 508. In the example of stimulation strategy 502, stimulation frames 506 and stimulation gaps 508 are shown to be of uniform size and to be interleaved in a one-to-one alternating pattern. This pattern will be understood to be but one illustrative possibility, and other relative lengths and temporal patterns for alternative stimulation strategies will be described in more detail below.

Stimulation strategy 502 may be used for various implementations of stimulation system 100, including hearing systems (e.g., any implementation 400 of hearing system 300-A), neuromodulation systems (e.g., an implementation of neuromodulation system 300-B), or the like. For example, given an implementation of stimulation system 100 that is configured to monitor a physiological condition using an implementation of stimulation device 102, stimulation strategy 502 may be specially designed or customized as a sensor-compliant (e.g., "sensor-friendly") stimulation strategy that is optimized for clean and efficient physiological condition monitoring. For example, stimulation strategy 502 may be configured to allow sensor data to regularly be detected (e.g., measured, recorded, etc.) during stimulation gaps 508 without interfering with stimulation being performed by stimulation device 102 during stimulation frames 506.

The length and frequency of stimulation frames 506 and stimulation gaps 508 may be determined based on parameters defining how a particular type of stimulation is to be effectively applied as well as how particular physiological conditions (e.g., any of the biometrics described herein) are to be effectively monitored. For example, for a cochlear implant system, it may be the case that each stimulation frame 506 is approximately 480 microseconds (µs) if it takes 40 µs to stimulate one channel (e.g., 20 µs per phase) and there are 16 channels in use. Other types of stimulation systems may use stimulation frames 506 that are similarly sized based on their own particular characteristics.

As another example, the lengths (e.g., pulse widths, durations, etc.) of stimulation gaps 508 may be sized in accordance with the type or types of physiological conditions that are to be monitored. For certain recipients and/or in certain hearing contexts (e.g., contexts associated with certain demands and/or intents of the recipient such as demands or intents to understand speech in a crowded room, etc.), it may be determined that any stimulation gap greater than approximately 1.0 millisecond (ms) would be noticeable and/or disruptive to the recipient. As such, the lengths of stimulation gaps may be kept to 1.0 ms or less in these examples. In contrast, for other recipients and/or hearing contexts (e.g., contexts associated with less stringent demands and/or intents of the recipient such as to sit and read in a quiet room, to sleep, etc.), it may be determined that stimulation gaps longer than 1.0 ms (e.g., stimulation gaps just longer than 1.0 ms or gaps much longer than 1.0 ms such as gaps several minutes or longer in certain contexts) are not disruptive or problematic to the recipient in the particular hearing context. As such, the lengths of stimulation gaps 508 in a stimulation strategy example such as this may be longer than 1.0 ms.

As another example, stimulation gaps 508 may be distributed in accordance with the type or types of physiological conditions that are to be monitored. For example, recording certain evoked potentials from the brain (e.g., cortical potentials, auditory potentials, etc.) may take measurements spanning approximately 1.0 second, so stimulation strategy 500 may schedule a plurality of gaps (e.g., 1.0 ms gaps to use one of the examples above) over a time period of 1.0 second to effectively capture this physiological condition. The data captured during this plurality of gaps may then be stitched together using techniques described below to represent the evoked potential during the course of the 1.0 second recording period. As another example, effective recording of certain heart-related biometrics may need to be performed over significantly longer periods of time, such as over minutes or hours. Accordingly, stimulation strategy 500 may include a plurality of gaps scheduled to span the necessary minutes or hours to effectively capture this physiological condition, and, again, the data captured during this plurality of gaps may be stitched together after recording to recreate the heart-related physiological condition. More or fewer stimulation gaps 508 of appropriate lengths may be employed for different types of physiological conditions and/or for embodiments in which a plurality of physiological conditions are to be monitored.

In the same or other examples, stimulation system 100 may determine that an EEG test is to be monitored every N number of milliseconds (or another suitable time period). Based on such measurement parameters, stimulation system 100 may determine whether it will be beneficial for the stimulation strategy to include stimulation gaps (e.g., stimulation-free blocks of time during which sensitive measurements may be made). Because no stimulation would be performed during such stimulation gaps, physiological condition detection performed during time that corresponds to stimulation gaps 508 would advantageously be free of artifacts even during normal operation of the stimulation system. In other words, the monitoring of the physiological conditions and the normal operation of the system (stimulating the recipient) would not interfere with one another since each would be limited to the stimulation frames and stimulation gaps built into the stimulation strategy.

Along with using the stimulation parameters and physiological condition properties to define stimulation strategy 502, stimulation system 100 may further define stimulation strategy 502 based on perceptual input or other characteristics (e.g., automatically-detected characteristics) of the recipient to thereby customize the stimulation strategy to the recipient. For instance, in order to determine a stimulation strategy such as stimulation strategy 502, stimulation system 100 may identify measurement parameters that may exist for a particular recipient and/or for a particular use case, system, or goal. Examples of how this may be done will be provided below.

Upon determining that stimulation gaps would be beneficial, one or more stimulation gaps of an appropriate size and frequency may be selected. For example, stimulation gaps 508 may be sized and located along timeline 504 in stimulation strategy 502 as shown. In some examples, this step of sizing and planning for stimulation frame and stimulation gaps may be more complex than the uniform alternating pattern of stimulation strategy 502. For instance, stimulation frames and stimulation gaps may be customized to preferences and characteristics of a particular recipient to ensure that physiological condition monitoring can be performed effectively and efficiently without interfering with normal stimulation operation of the system.

Figure 6:
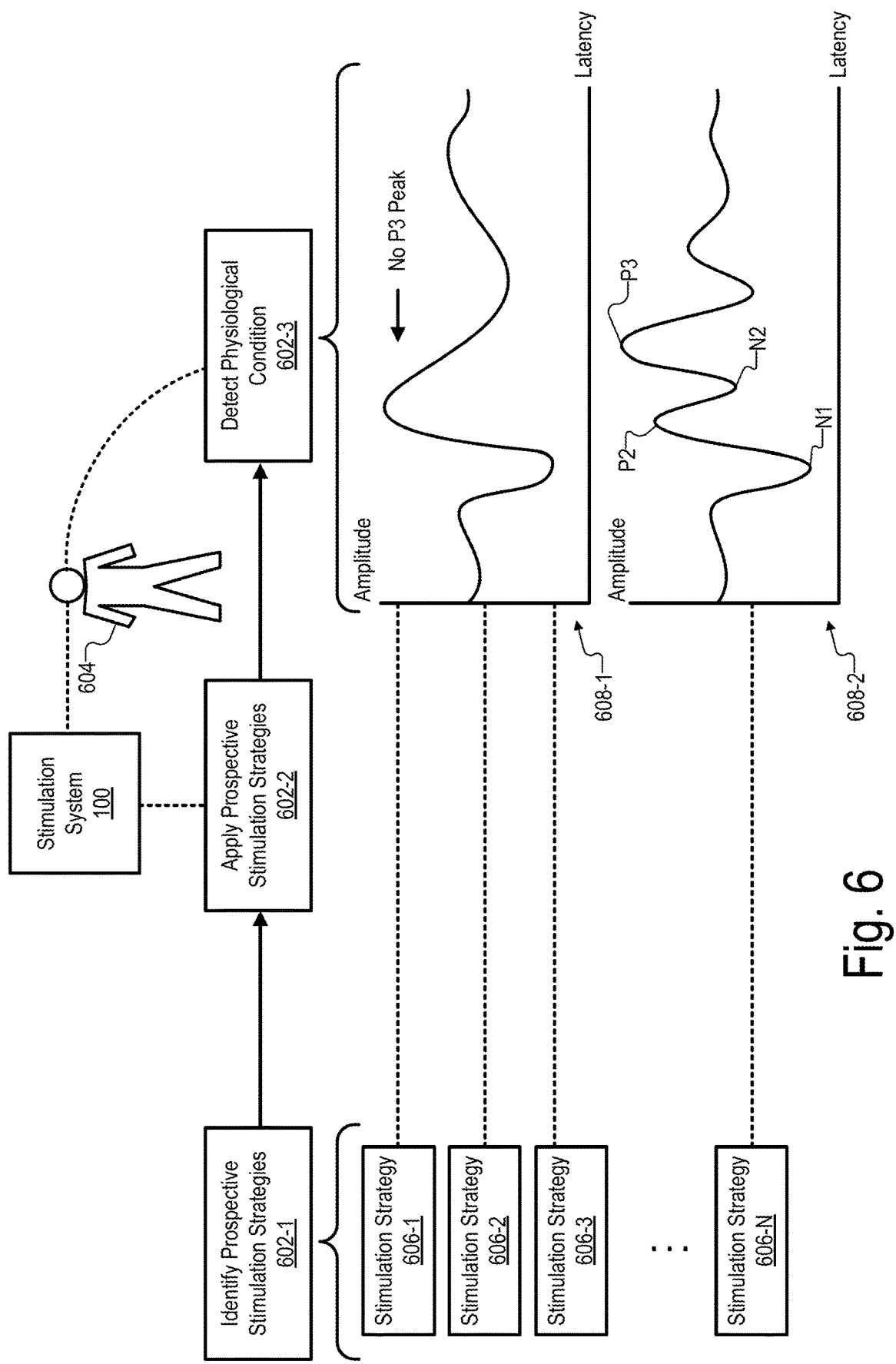
FIGS. 6-7 show illustrative aspects of how a stimulation system may determine a stimulation strategy that is customized to a recipient of the stimulation system.
Figure 7:
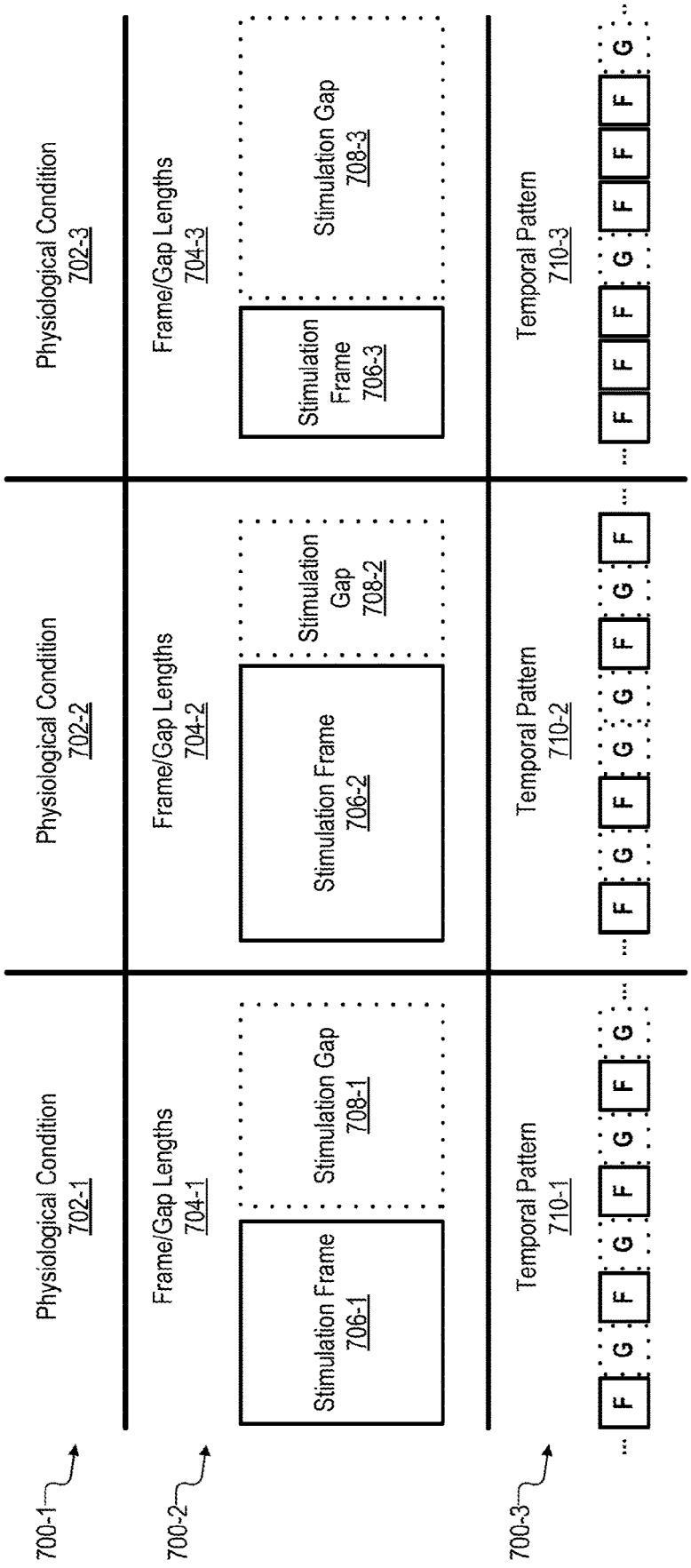

To illustrate, FIGS. 6-7 show various illustrative aspects of how an implementation of stimulation system 100 may determine a stimulation strategy that is customized to a recipient of the system. Specifically, FIG. 6 illustrates how the determining of a stimulation strategy may include customizing the stimulation strategy to the recipient based on a test applied to the recipient to automatically determine characteristics perceived by a brain of the recipient with respect to one or more prospective stimulation strategies presented to the recipient. FIG. 7 illustrates how the determining of the stimulation strategy may be performed as a series of operations such as 1) identifying a type of physiological condition that is to be detected; 2) selecting (e.g., based on the identified type of physiological condition) a length of the stimulation frames and a length of the stimulation gaps; and 3) determining (e.g., based on the identified type of physiological condition and a characteristic of the recipient) a temporal pattern for the stimulation gaps and the stimulation frames.

In FIG. 6, a series of stages 602 (i.e., stages 602-1 through 602-3) are shown to be included in the customizing of a stimulation strategy to a recipient 604. As shown, at a first stage 602-1, stimulation system 100 may identify a plurality of prospective stimulation strategies 606 (e.g., stimulation strategies 606-1 through 606-N). Prospective stimulation strategies 606 are labeled as stimulation strategies 606-1 through 606-N in FIG. 6 for clarity and convenience of description (e.g., to indicate that the strategies are different from one another and to allow each strategy to be individually referred to in this description). However, it will be understood that it may not always be the case that a plurality of N prospective stimulation strategies are identified at stage 602-1. For example, in certain implementations, one or more rules for adjusting a stimulation strategy to form different prospective stimulation strategies (e.g., a rule to gradually increase the length of stimulation gaps within the stimulation strategy, a rule to gradually increase the frequency of stimulation gaps within the stimulation strategy, etc.) may be employed at stage 602-1 and prospective stimulation strategies 606 may be iteratively created on an as-needed basis as stages 606-2 and 606-3 are performed.

At a second stage 602-2, each of prospective stimulation strategies 606 may, one at a time, be applied to recipient 604 by stimulation system 100. Then, at a third stage 602-3, a physiological condition of recipient 604 may be detected to allow the system to analyze the performance of the prospective stimulation strategy 606 that is being applied. For example, it will be assumed that stimulation gaps in lower numbered stimulation strategies 606 are short, and that the length of the stimulation gaps increases slightly with each higher-numbered stimulation strategy 606. Accordingly, as shown, when prospective stimulation strategy 606-1 is applied at stage 602-2, a physiological condition 608-1 (results of an EEG test in this example) may be detected at stage 602-3. Because a P3 peak (also referred to as a P300 peak) is not detected in the EEG test results of physiological condition 608-1 for this prospective stimulation strategy ("No P3 Peak"), it may be determined that recipient 604 is not able to perceive the stimulation gaps included within prospective stimulation strategy 606-1. In other words, prospective stimulation strategy 606-1 may be a suitable stimulation strategy at least as far as its lack of perceivable interference with stimulation during normal operation. However, it may be desirable, if recipient 604 would not be negatively affected, for the stimulation gaps to be longer than the gaps included in stimulation strategy 606-1.

Accordingly, a second prospective stimulation strategy 606-2 that has slightly longer stimulation gaps may be applied next at stage 602-2. As indicated by the dotted line from stimulation strategy 606-2 to physiological condition 608-1, it may be determined at stage 602-3 that, here again, the P3 peak is not evoked in recipient 604, thereby indicating that prospective stimulation strategy 606-2 likewise does not interfere with normal operation as far as is perceivable by the brain of recipient 604. One or more additional such prospective stimulation strategies 606 (e.g., including stimulation strategy 606-3) may likewise be iteratively tried out in this way until, eventually, one of the prospective stimulation strategies 606 has stimulation gaps that are long enough to be perceived by recipient 604. This situation is illustrated by stimulation strategy 606-N, which, as shown by the dotted line extending from the strategy, connects to a physiological condition 608-2 showing EEG test results in which the P3 peak is detected. At this point, stimulation system 100 may determine that the brain of recipient 604 would be able to perceive or notice stimulation gaps of the length included in stimulation strategy 606-N, such that these stimulation gaps could interfere with normal operation of the cochlear implant system and may thus be undesirable. Accordingly, the previous prospective stimulation strategy 606 (i.e., the strategy having the longest stimulation gaps that do not evoke the P3 peak in recipient 604) may be automatically selected as the stimulation strategy that is customized to recipient 604 and that is to be used going forward. In certain examples, this type of testing and stimulation strategy determination may be performed on a channel-by-channel or electrode-by-electrode basis, and/or may be performed dynamically (on the fly) during normal operation.

Automatic customization of the stimulation strategy such as illustrated in FIG. 6 may be useful in various situations and for various reasons. As one example, the technique shown in FIG. 6 may allow for a stimulation strategy to be efficiently and accurately customized to recipients who have difficulty or are not capable of providing behavioral input (e.g., infants and children, recipients with certain disabilities, etc.). As another example, the technique shown in FIG. 6 may be performed automatically from time to time without needing to be directed or facilitated by a clinician (e.g., including when the recipient is not present at a clinic) and, in some examples, without recipient 604 even needing to be consciously aware that the test is occurring. In this way, appropriate stimulation strategies may be automatically and dynamically determined in a variety of different contexts and situations. For example, it may be advantageous for a different stimulation strategy to be used when recipient 604 is in a quiet room and exerting a high degree of focus and when recipient is in a noisy room, or is asleep, or under various other circumstances. Additionally, it will be understood that, while this automatic customization provides many benefits, certain implementations may employ behavioral input in addition, or as an alternative, to the automatically detected physiological conditions 608 shown in FIG. 6. For instance, the behavioral input may include verbal or other subjective input consciously provided by recipient 604 if he or she is able to reliably do so. Such input may be used in combination with physiological conditions 608 in certain implementations, and may take the place of physiological conditions 608 in other implementations.

In FIG. 7, several operations 700 (i.e., operations 700-1 through 700-3) are illustrated in rows of a grid. For each operation 700, columns of the grid represent different examples that may be associated with different physiological conditions 702 (e.g., physiological conditions 702-1 through 702-3 in the example of the three columns illustrated in FIG. 7). In some examples, customizing a stimulation strategy may include performing each of operations 700 with respect to a physiological condition 702 that is detected for a recipient. In some examples, operations 700 may be performed instead of the customization technique described above in relation to FIG. 6. In other examples, operations 700 may be integrated as part of that technique. For instance, operations 700 may be performed as part of the identification of prospective stimulation strategies at stage 602-1 or may be performed to optimize a selected stimulation strategy selected after stages 602-2 and 602-3 are complete.

At operation 700-1, stimulation system 100 may identify a type of physiological condition that has been or is to be detected. In certain examples, the target physiological condition that is to be detected may be identified as a physiological condition that is detected using a sensing device 106 that is also used as a stimulation device 102 (e.g., a cochlear implant electrode that is used for stimulating the recipient and for performing EEG tests to monitor a physiological condition, etc.) or that is known to interfere with or to receive interference from the stimulation device. In these cases, a stimulation strategy having stimulation frames and stimulation gaps may be needed and stimulation system 100 may proceed to perform operations 700-2 and 700-3. In other examples, the target physiological condition that is to be detected may be identified as a physiological condition that is detected using only dedicated sensing devices 106 that do not interfere with or receive interference from a stimulation device 102. In these cases, a stimulation strategy may not necessarily involve stimulation frames and stimulation gaps, such that operations 700-2 and 700-3 may be bypassed.

Certain physiological conditions identified at operation 700-1 may be most efficiently and effectively detected using different types of measurement patterns. For instance, certain physiological conditions may require longer blocks of time to properly detect while other physiological conditions may be effectively detected using shorter blocks of time. As another example, physiological conditions that remain relatively static may be effectively detected with a relatively low frequency, while more dynamic physiological conditions may need to be detected more often. As will be described in more detail below, each physiological condition 702 may represent a physiological condition with different types of characteristics that may be best served by a different stimulation strategy.

At operation 700-2, stimulation system 100 may select a length of the stimulation frames and a length of the stimulation gaps that are to be used for the type of physiological condition identified at operation 700-1. In some examples, the length of each stimulation gap may be a uniform length, while, in other examples, varying lengths for different stimulation gaps may be selected. As shown, based on physiological condition 702-1, a frame/gap length 704-1 indicates that the stimulation frame and stimulation gap lengths may be equal. This is illustrated by a stimulation frame 706-1 and stimulation gap 708-1 that are illustrated as having an equal length in FIG. 7. In contrast, a frame/gap length 704-2 indicates that, based on physiological condition 702-2, a stimulation frame 706-2 may be considerably longer than a stimulation gap 706-2. As yet another example, a frame/gap length 704-3 in FIG. 7 indicates that, based on physiological condition 702-3, a stimulation frame 706-3 may be shorter than a stimulation gap 708-3.

At operation 700-3, stimulation system 100 may determine a temporal pattern 710 (e.g., one of temporal patterns 710-1 through 710-3) for the stimulation gaps 708 and stimulation frames 706 whose lengths were selected at operation 700-2. Operation 700-3 may be performed based on the type of physiological condition 702 identified at operation 700-1, as well as based on one or more characteristics of the recipient such as characteristics related to what the recipient is capable of perceiving (e.g., as determined behaviorally and/or using a technique such as described above in relation to FIG. 6). In some examples, the temporal pattern 710 determined at operation 700-3 may periodically locate stimulation gaps throughout the stimulation strategy at set intervals of time. For instance, as shown in temporal pattern 710-1, stimulation gaps 708-1 (labeled "G") may be interleaved in a one-to-one alternating pattern with stimulation frames 706-1 (labeled "F") for physiological condition 702-1. In other examples, the temporal pattern 710 determined at operation 700-3 may locate stimulation gaps in a non-periodic manner or may call for one-off (e.g., one time only) stimulation gaps such as on an as-needed basis. For instance, as shown in temporal pattern 710-2, stimulation gaps 708-2 may be inserted in a non-periodic or as-needed pattern between stimulation frames 706-2 for physiological condition 702-2. Temporal pattern 710-3 shows another periodic example in which stimulation gaps 708-3 are placed relatively infrequently between groups of several consecutive stimulation frames 706-3.

It will be understood that any suitable frame/gap lengths 704 and/or temporal patterns 710 may be employed as may best serve different types of physiological condition monitoring that are to be performed and/or different monitoring goals that stimulation system 100 aims to achieve. For example, as has been described, certain implementations may monitor multiple types of physiological conditions (e.g., multiple physiological conditions 702) and may size stimulation frames 706, size stimulation gaps 708, and define and schedule out temporal patterns 710 accordingly. For any frame/gap lengths or temporal patterns that may be selected or determined for a given stimulation strategy, it may be desirable that the stimulation gaps are not perceivable by the recipient or detrimental to the performance of the cochlear implant system.

In some examples, a physiological condition that is to be measured or monitored may be detected relatively quickly and all at once. In these examples, the time that corresponds to the stimulation gaps during which the physiological condition is detected may thus include time corresponding to only a single stimulation gap.

Figure 8A:
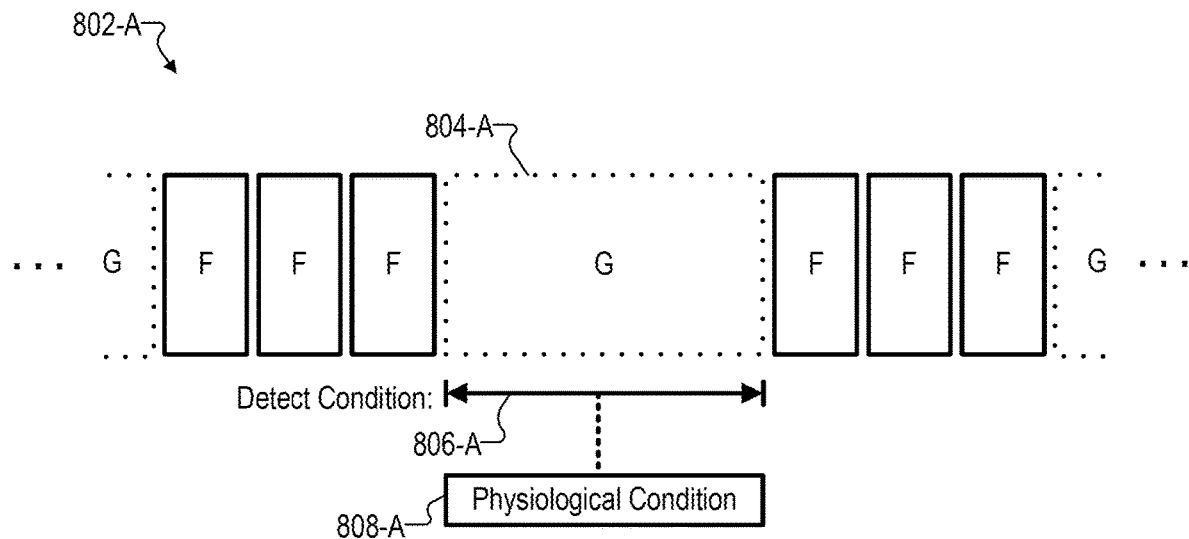
FIGS. 8A-8B show illustrative aspects of how physiological conditions of a stimulation system recipient may be detected with respect to different stimulation strategies.

To illustrate, FIG. 8A shows illustrative aspects of how a physiological condition of a recipient may be detected with respect to a stimulation strategy 802-A that includes groupings of relatively short stimulation frames (each denoted by an "F") separated by a relatively long stimulation gap 804-A (denoted by a "G"). As illustrated, a physiological condition 808-A may be detected all at once within a detection time block 806-A of stimulation gap 804-A in this example.

In contrast, other examples of physiological conditions that are to be detected in certain implementations may not be able to be fully detected within an amount of time that can reasonably be allotted to a single stimulation gap. For instance, certain slow-moving or long-latency alpha waves that may be detected by an EEG may take place over a relatively long period of time, such that if a single stimulation gap were created to capture the entire brain wave, it would interfere noticeably and detrimentally with normal stimulation operation of the cochlear implant system (e.g., by causing the stimulation frames to be far enough apart that the stimulation to the user would be compromised). In these examples, the time that corresponds to the stimulation gaps during which the physiological condition is detected may thus include time corresponding to two or more stimulation gaps that are separated by at least one stimulation frame. The detecting of the physiological condition may then include combining (e.g., stitching together or otherwise joining during a post-processing phase, etc.) data that is detected during each of the two or more stimulation gaps.

Figure 8B:
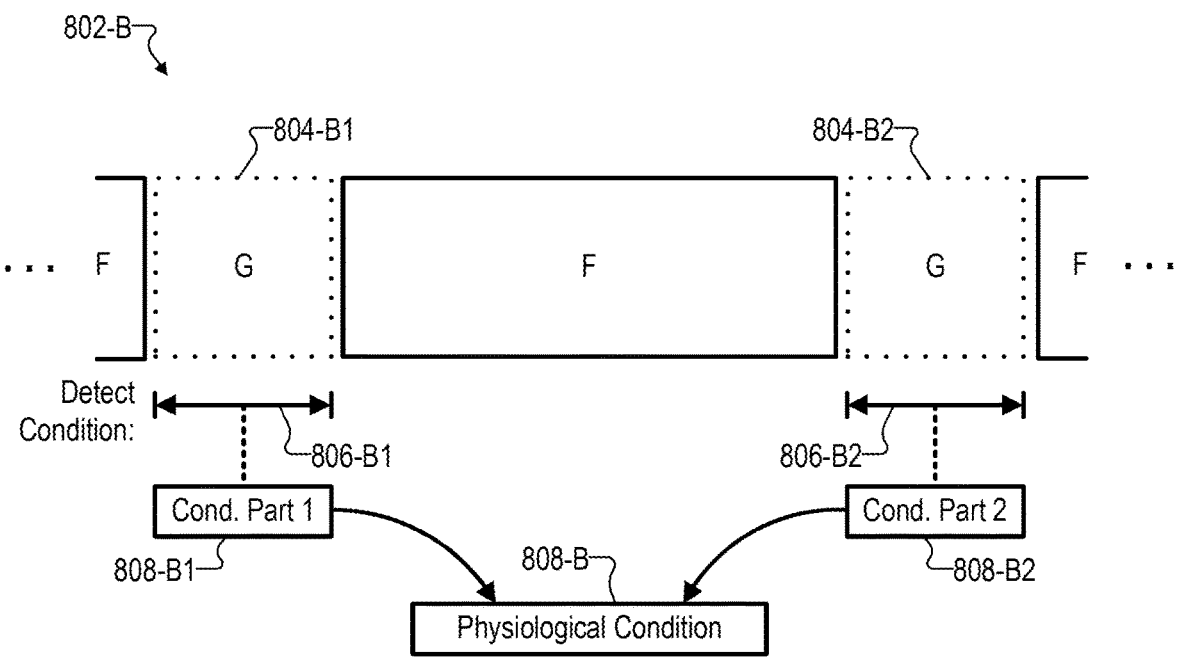

To illustrate, FIG. 8B shows illustrative aspects of how physiological conditions of a recipient may be detected with respect to a stimulation strategy 802-B that includes a relatively long stimulation frame (denoted by an "F") and relatively short stimulation gaps 804-B1 and 804-B2 (each denoted by a "G") that are separated by the stimulation frame. As illustrated, a physiological condition 808-B may be detected in two parts labeled 808-B1 ("Cond. Part 1") and 808-B2 ("Cond. Part 2") over the course of two separate detection time blocks 806-B1 and 806-B2. These separate parts 808-B1 and 808-B2 are detected, respectively, during the different and separated time blocks 806-B1 and 806-B2. However, the parts are later combined (e.g., stitched together) to form physiological condition 808-B, as shown.

Figure 9:
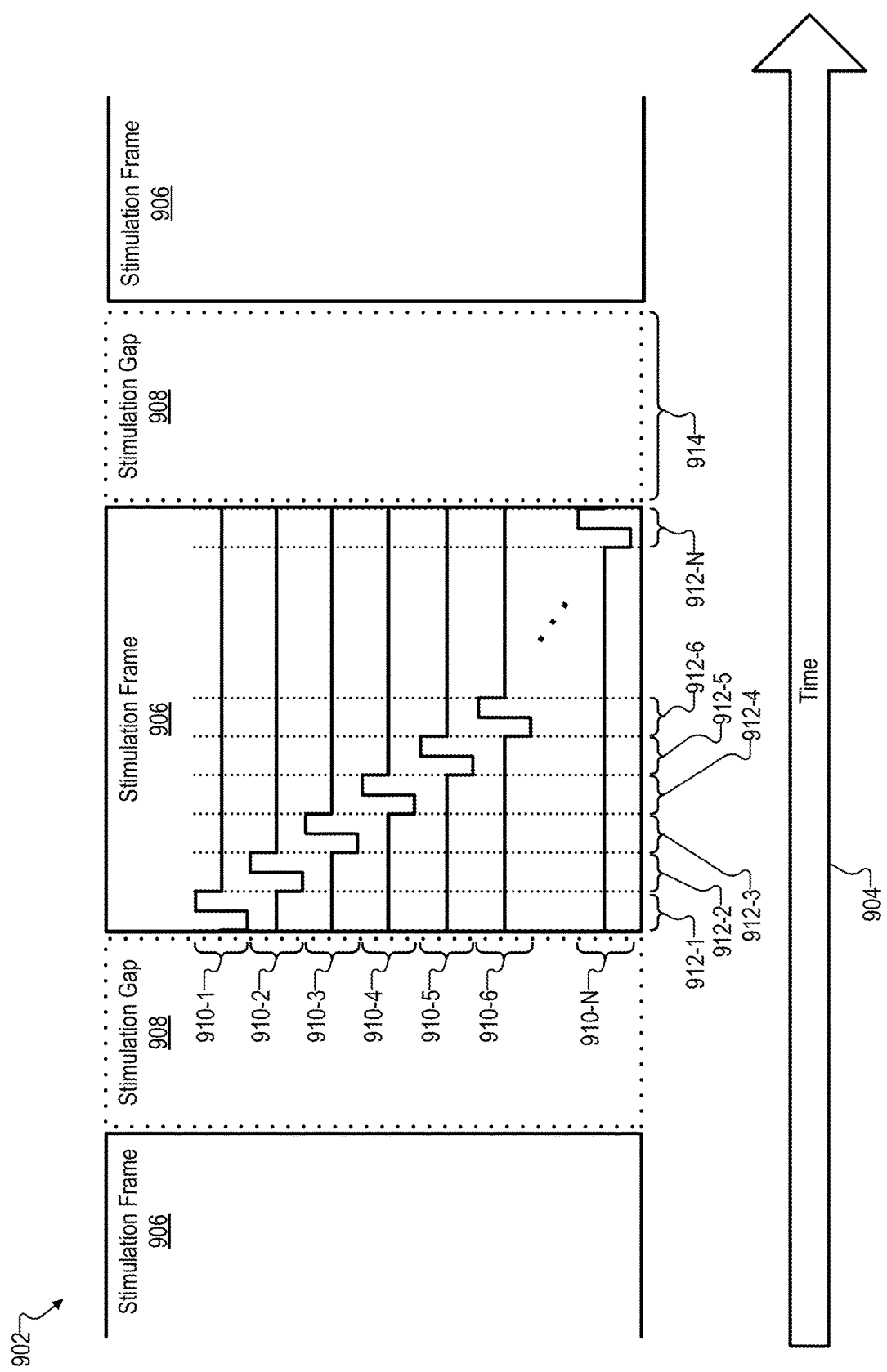
FIG. 9 shows an illustrative stimulation strategy for monitoring a physiological condition of a cochlear implant system recipient.

FIG. 9 shows an illustrative stimulation strategy 902 for monitoring a physiological condition of a cochlear implant system recipient. Up to this point, each of the stimulation strategies illustrated and described herein have been understood to refer to general stimulation strategies applicable to any of various implementations of stimulation system 100. The focus has been in describing how physiological condition monitoring may be performed during stimulation gaps and how stimulation gaps and stimulation frames may be strategically planned for to allow concurrent physiological condition monitoring during uninterrupted operation of the stimulation system. In the example of FIG. 9, certain aspects particular to a cochlear implant system such as cochlear implant system 400-A or an implementation thereof are shown to illustrate how the system may be configured to operate over a period of time 904 during an illustrative stimulation frame 906.

As shown, a plurality of stimulation frames 906 are interleaved to alternate with a plurality of stimulation gaps 908. During stimulation frames 906, the cochlear implant system may perform stimulation operations in the ways that will now be described. During stimulation gaps 908, the cochlear implant system may perform physiological condition monitoring operations in any of the ways that have been described above.

In an implementation of a cochlear implant system that performs stimulation strategy 902, each electrode of the array of electrodes included in the cochlear implant system may be assigned to at least one channel 910 in a plurality of channels 910 (e.g., channels 910-1 through 910-N) that is used by the cochlear implant to apply stimulation to a recipient of the cochlear implant system. In some examples, a given channel 910 may be associated with a single electrode configured to apply electrical stimulation associated with a particular frequency to a particular part of the cochlea of the recipient. In other examples, a given channel 910 may be associated with a plurality of electrodes configured to collectively and cooperatively apply electrical stimulation associated with a particular frequency to a particular part of the cochlea.

In stimulation strategy 902, each stimulation frame 906 may include a plurality of consecutive time blocks 912 (e.g., time blocks 912-1 through 912-N) during which the plurality of channels 910 applies the stimulation one channel at a time in sequence. Specifically, as shown in FIG. 9, channel 910-1 may apply stimulation during time block 912-1 (while not applying stimulation during the remainder of time blocks 912), channel 910-2 may apply stimulation during time block 912-2 (while likewise not applying stimulation during the remainder of time blocks 912), channel 910-3 may apply stimulation during time block 912-3 (while also abstaining from applying stimulation during the other time blocks 912), and so forth. Each stimulation gap 908 of stimulation strategy 902 may include a time block during which all of channels 910 abstain from applying the electrical stimulation (e.g., so as to allow for detection of physiological conditions without interference). For example, as shown, a time block 914 is shown for one of stimulation gaps 908 to illustrate the time when the cochlear implant system may be configured to detect the physiological condition.

The one-at-a-time stimulation pattern of stimulation frames 906 in FIG. 9 will be understood to be only an example of the types of stimulation frames that may be implemented by a cochlear implant system such as cochlear implant system 400-A. For instance, in other examples, more than one channel 910 may apply stimulation at once, channels 910 may apply stimulation at more than one instance within a particular stimulation frame 906, the order in which channels 910 apply the stimulation may be different than the order shown (or may change from frame to frame), and so forth. Additionally, as been described and illustrated, the temporal pattern of stimulation frames and stimulation gaps may be other than what is shown in stimulation strategy 902. For instance, each stimulation gap 908 may separate groupings of several consecutive stimulation frames 906 in certain implementations.

As has been described, once a physiological condition has been detected, stimulation system 100 may perform an action based on the detected physiological condition. In some examples, the action may be performed as the physiological condition continues to be monitored and as stimulation continues to be applied to the recipient.

Figure 10:
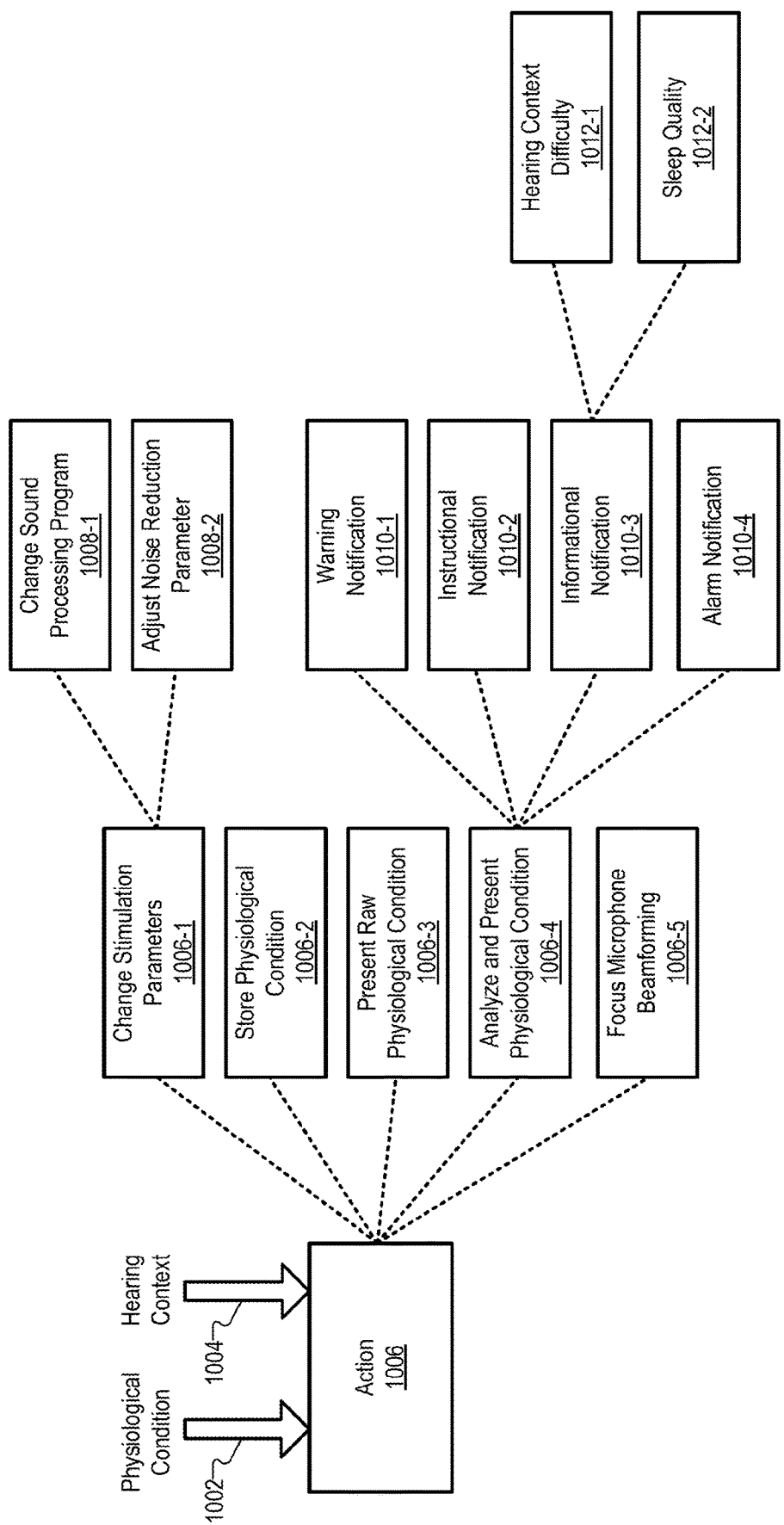
FIG. 10 shows various actions that may be performed based on a detected physiological condition of a stimulation system recipient.

To illustrate, FIG. 10 shows illustrative aspects of various actions that may be performed based on a detected physiological condition 1002 of a hearing system recipient. Specifically, based on physiological condition 1002, as well as based on other suitable data such as a hearing context 1004 in certain hearing system implementations, stimulation system 100 may perform an action 1006. Physiological condition 1002 may be detected in any of the ways described herein and may be used as a basis for the action 1006 that is to be performed, as will be made apparent by the actions described below. In applicable implementations (e.g., hearing system implementations), hearing context 1004 may also influence what action is performed and/or how the action 1006 is performed, as will be described below. Additionally, each of a plurality of specific actions 1006 (e.g., actions 1006-1 through 1006-5) will also be described, along with specific implementations thereof that are labeled as actions 1008 (e.g., actions 1008-1 and 1008-2), actions 1010 (e.g., actions 1010-1 through 1010-4), and actions 1012 (e.g., actions 1012-1 and 1012-2).

In certain hearing system implementations of stimulation system 100, a classification system (also referred to as a "classifier") may be included to classify hearing context 1004 based on input audio detected by a microphone and/or other input data that is received. For example, the microphone may be implemented by microphone 310 (or an implementation thereof such as microphone 420 or 430) and configured to detect sound that is presented to the recipient, while the classifier may be integrated within processing unit 108 or an implementation thereof (e.g., processing unit 302-A, processing unit 408, sound processor 418, computing device 424, hearing aid 428, etc.) and configured to classify hearing context 1004 for the recipient based on the sound detected by the microphone. The classifier may determine, for instance, whether the recipient is in a quiet room context, a noisy room context, a one-on-one conversation context, a music listening context, and/or any of various other potential hearing contexts.

Stimulation system 100 may perform the action 1006 based on hearing context 1004 that has been detected for the recipient by the classifier. For instance, based on hearing context 1004, stimulation system 100 may select an optimal time to detect physiological conditions (e.g., a time that will be relatively low impact on the recipient). As one example, if hearing context 1004 indicates that the recipient is in a quiet room (e.g., an environment associated with a low sound pressure level ("SPL")), stimulation system 100 may determine that longer stimulation gaps would be appropriate to add to the stimulation strategy or even that stimulation frames may be temporarily discontinued for a period of time while certain physiological conditions are measured and monitored. As another example, if hearing context 1004 indicates that the recipient is in the middle of a one-on-one conversation or in a noisy room, stimulation system 100 may determine that it is not an appropriate time to sacrifice any stimulation frames to provide stimulation gaps for physiological condition monitoring. In still other examples that will be made apparent below, various actions 1006 may be performed in response to, or in a manner that directly accounts for, hearing context 1004 provided by the classifier.

Action 1006-1 is one example of an action 1006 that may be performed based on physiological condition 1002 and/or hearing context 1004. As shown in FIG. 10, action 1006-1 may involve changing one or more stimulation parameters of stimulation system 100 to alter the way that any of the components of stimulation system 100 (e.g., including components of stimulation device 102) operate to better account for the condition of the recipient and/or the hearing context of the recipient's environment.

As one example of the types of parameters that may be changed for a hearing system implementation such as hearing system 300-A, action 1008-1 illustrates an action that automatically changes a sound processing program being used to direct an implementation of stimulation device 304-A (e.g., cochlear implant 402, loudspeaker 432, etc.) to apply electrical and/or acoustic stimulation to the recipient of stimulation system 100. It may be helpful for the sound processing program to be changed, for example, when the recipient is in a noisy hearing context and is detected to be experiencing high levels of stress (e.g., based on the heart rate variability of the recipient, as described above), or under other suitable circumstances.

As another example of how parameters may be changed to implement action 1006-1 for hearing system implementations, action 1008-2 represents a noise reduction parameter that may be adjusted. For instance, the physiological condition 1002 that has been detected may relate to alpha waves that have been detected and from which may be derived an average rate at which the eyes of the recipient are blinking. Based on this blink rate (e.g., and how the blink rate compares to one or more predetermined blink rate thresholds, etc.), an attentiveness level of the recipient may be determined. For example, it may be determined that the recipient is highly focused or is not particularly focused on sound currently being presented. Action 1008-2 may be performed based on the attentiveness level (e.g., based on the average rate at which the eyes of the recipient are blinking) and may involve adjusting a noise reduction parameter of stimulation system 100 in accordance with the attentiveness level of the recipient. For instance, if the recipient is highly attentive and focused (e.g., as evidenced by a relatively low blink rate), the noise reduction parameter may be increased to assist the recipient in paying attention to a single sound source, while, if the recipient is determined to not be particularly attentive or focused (e.g., as evidenced by a relatively high blink rate), the noise reduction parameter may be decreased to assist the recipient in hearing sound from various sources in the environment.

The blink rate and attentiveness level derived from physiological condition 1002 may be combined with information derived from hearing context 1004 to help make determinations about how to adjust the noise reduction parameter or other cochlear implant system parameters. For example, stimulation system 100 may determine that the recipient is in a speaking situation in a noisy environment (based on hearing context 1004) and that the recipient is feeling stress as a result (based on physiological condition 1002). In response to this determination, stimulation system 100 may automatically increase the noise reduction parameter, lower the volume or intensity of stimulation, provide a soothing stimulus to help the patient calm down, or perform another such parameter adjustment.

For stimulation system implementations that are not hearing systems (e.g., neuromodulation system 300-B or other suitable stimulation systems), it will be understood that analogous stimulation parameter changes may be implemented by an action such as action 1006-1.

Action 1006-2 is another example of an action 1006 that may be performed based on physiological condition 1002 and/or hearing context 1004. As shown in FIG. 10, action 1006-2 may involve logging away or otherwise storing data representative of physiological condition 1002 for later reference by stimulation system 100, by the recipient, or by a caretaker of the recipient such as a clinician tracking the recipient's progress and experience with stimulation system 100. In some examples, action 1006-2 may involve compacting (e.g., compressing, encoding, etc.) the data that is to be stored in any manner as may serve a particular embodiment. Some filtering may also be implemented by action 1006-2. For instance, stimulation system 100 may be configured to store only physiological conditions that are deemed to be significant, such as, for example, storing only the amplitude of detected alpha waves whenever there is a large change. In certain implementations, log entries in which physiological conditions are stored may also include other relevant data such as time stamps of when the physiological conditions were detected or the like.

Action 1006-3 is yet another example of an action 1006 that may be performed based on physiological condition 1002 and/or hearing context 1004. As shown in FIG. 10, action 1006-3 may involve presenting raw data representative of physiological condition 1002 to the recipient or to a caretaker of the recipient such as the clinician tracking the recipient's progress and experience with stimulation system 100. In some examples, the presenting of physiological condition 1002 data at action 1006-3 may be performed in real time immediately after physiological condition 1002 is detected. As with the data logged by action 1006-2, the data presented by action 1006-3 may be "raw" measurement data that has been detected (e.g., a heart rate, etc.) rather than health or sentiment determinations that are derived from the raw measurements. For example, computing device 424 (e.g., a mobile application, etc.) may present a real time heart rate of the recipient in the example of cochlear implant system 400-C or a similar implementation of another type of stimulation system.

In contrast, action 1006-4 shows yet another example of an action 1006 in which analysis of raw data is performed for the presentation of physiological condition 1002. However, in this example, an analysis of physiological condition 1002 and/or hearing context 1004 may be performed to make determinations (i.e., derive conclusions) about the health, sentiment, and/or behavior of the recipient, and these determinations may be presented to the user (e.g., the recipient, the clinician, etc.) in various ways to implement action 1006-4.

As one example of how analyzed physiological condition data may be presented to a user, action 1010-1 represents a notification that may be provided to issue a warning or otherwise indicate that an issue has been detected regarding the health or wellbeing of the recipient or the stimulation system. For instance, physiological condition 1002 may be indicative of an issue being experienced by the recipient and data representative of this physiological condition may be configured to notify a user (e.g., the recipient himself or herself, a caretaker of the recipient such as a guardian or clinician, etc.) of the issue being experienced by the recipient. As an example, stimulation system 100 may identify heart-related issues based on a heart rate variability that has been detected. In response, a notification generated as part of action 1010-1 may be issued by way of the Physician Quality Reporting System ("PQRS") to give medical professionals the opportunity to assess the quality of care being provided to the recipient and to ensure that the recipient gets the right care at the right time. As another example, the notification of action 1010-1 may involve auditory, haptic, or other suitable alerts or warnings when stimulation system 100 detects that physiological conditions (e.g., heart rate variability, stress or other conclusions derived based on the raw physiological measurements) are out of range or indicative of a disease state. For instance, if stimulation system 100 is a hearing system, acoustic or electrical stimulation may be applied directly to the recipient to create a sound indicative of the alert.

In some examples, EEG monitoring may be used to provide neurofeedback of alpha/theta wave oscillation. Accordingly, stimulation system 100 may be configured to provide a recipient an audio alert or other suitable feedback (e.g., any of the notifications described herein) based on the detected alpha/theta oscillation. These types of alerts or notifications may allow recipients to become more conscious of their own stress levels, such as by indicating the stress level (e.g., on a mobile application that indicates a stress level on a scale from 1-5 or another suitable scale). In some examples, stimulation system 100 may provide alerts when the stress level crosses a threshold. For instance, for neuromodulation system implementations, neuromodulation stimulation (neurofeedback) may be provided to recipients to help treat conditions such as tinnitus, epilepsy, or other conditions from which the recipient may suffer (including various conditions mentioned above).

As another example of how analyzed physiological condition data may be presented to a user, action 1010-2 shows a notification that may be provided to instruct a user (e.g., the recipient or a caretaker thereof) about an action that the user is to perform to mitigate or otherwise address an issue that has been identified based on physiological condition 1002. For instance, physiological condition 1002 may be indicative of an issue being experienced by the recipient and data representative of this physiological condition may be configured to advise a course of action that the user is to take to address the issue being experienced by the recipient. As an example, if stimulation system 100 detects that the recipient is stressed and it is effecting the recipient's heart rate, the notification issued as part of action 1010-2 may instruct the recipient to take a break from what he or she is doing, to take a few deep breaths to calm down, or to otherwise try to calm himself or herself in any suitable way. In some examples, along with an instruction to calm down, the instructional notification delivered at 1010-2 may be provided together with soothing stimulus (e.g., calming music, a favorite sound of the recipient, etc.) that may configured to help the recipient relax.

As another example of how analyzed physiological condition data may be presented to a user, action 1010-3 represents a notification that may provide helpful information to the user. In these examples, physiological condition 1002 may not necessarily indicate that an undesirable health or sentiment condition has been detected, but, rather, may be associated with information that may be of interest to the user.

As one example, action 1012-1 may represent an informational notification that is provided when hearing context 1004 indicates a difficulty of the hearing situation the recipient is in. Action 1012-1 may implement action 1010-3 by providing a notification to the recipient indicating the difficulty of the hearing situation (e.g., how subjectively difficult the hearing context of the environment has been detected to be). In certain situations, a hearing system recipient may be stressed in large part because he or she feels that his or her difficulty in hearing is unique to the recipient due to his or her hearing loss. As such, the recipient may be made to feel more confident and less stressed by knowing that the scene is simply a noisy and difficult situation for everyone regardless of their natural hearing ability.

As another example, action 1012-2 represents an informational notification that may be provided when physiological condition 1002 is detected as the recipient sleeps. In certain examples, physiological condition monitoring may be performed as the recipient sleeps (e.g., for implementations of stimulation system 100 configured to be operational even during the night). Based on such physiological conditions, stimulation system 100 may determine how well the recipient is sleeping, how long the recipient has been sleeping, what stages of sleep the recipient passes through (together with timestamps for each change in sleep stage), and so forth. As a result, notifications may be provided to implement action 1010-3 to indicate a sleep quality of the recipient (e.g., how long the recipient slept, how well the recipient slept, how much time was spent in each different sleep stages, etc.).

As another example of how analyzed physiological condition data may be presented to a user at action 1006-4, action 1010-4 represents an alarm notification that may be provided to, for example, wake the recipient from sleep or remind the user of a scheduled appointment. Here again, the detected physiological condition 1002 in this example may not necessarily indicate that any undesirable health or sentiment condition has been detected. Rather, for instance, if the detecting of physiological condition 1002 is performed while the recipient is asleep, action 1010-4 may involve providing an alarm to wake the recipient from sleep based on physiological condition 1002. As an example, the physiological condition 1002 may indicate that the user is in a particular stage of sleep that is easier to be woken from (e.g., a light stage of sleep rather than a deep stage of sleep) and may provide the alarm based on that determination (rather than providing the alarm when the user is in a deeper stage of sleep). As another example, the physiological condition 1002 may relate to the fact that the recipient is sleeping and, as the physiological condition 1002 is continuously monitored, stimulation system 100 may track how long the recipient has slept such that the alarm of action 1010-4 may be provided to wake the recipient only after the recipient has gotten sufficient sleep (e.g., an amount that the recipient has preset as a desirable amount of sleep, such as 8 hours). Such alarms and notifications provided by actions 1010-3 and 1010-4 may help the recipient improve his or her sleep and improve his or her sentiment because of the good amount of sleep he or she achieved and the way that he or she was awoken.

Action 1006-5 is yet another example of an action 1006 that may be performed based on physiological condition 1002 and/or hearing context 1004. As shown in FIG. 10, action 1006-5 may involve focusing microphone beamforming based, for example, on where the recipient is detected to be looking. For instance, in an implementation in which stimulation system 100 includes a microphone configured to detect sound presented to the recipient (e.g., a hearing system implementation such as hearing system 300-A or any implementation thereof), physiological condition 1002 may indicate that the eyes of the recipient are looking in a particular direction (e.g., to the left, to the right, etc.) and action 1006-5 may be a beamforming action with respect to the microphone to focus the microphone in the particular direction that the eyes of the recipient are looking. More specifically, EEG monitoring may allow for the eyes of the recipient to be tracked, since certain brain waves detected as part of the EEG monitoring may indicate that the recipient is looking to the left while other brain waves may indicate that the recipient is looking to the right. Accordingly, stimulation system 100 may track the primary speaker talking to the recipient using EEG via speech envelope tracking and/or the EEG monitoring of the eye movements. Based on these indications, stimulation system 100 may perform action 1006-5 to implement neurosteering operations in which front-end processing of incoming audio is steered to focus on speech coming from the primary speaker. Action 1006-5 may additionally or alternatively involve controlling the microphone directionality to aim directional microphones toward the primary speaker (e.g., using beamforming techniques, etc.).

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a stimulation device configured to apply stimulation to a recipient;
   a sensing device configured to detect a physiological condition of the recipient; and
   a processing unit communicatively coupled to the stimulation device and the sensing device and configured to:
   determine a stimulation strategy that is customized to the recipient and includes stimulation frames and stimulation gaps, the determining of the stimulation strategy including:
   identifying a type of physiological condition that is to be detected,
   selecting, based on the identified type of physiological condition, a length of the stimulation frames and a length of the stimulation gaps, and
   determining, based on the identified type of physiological condition and a characteristic of the recipient, a temporal pattern for the stimulation gaps and the stimulation frames,
   direct the stimulation device to apply the stimulation to the recipient in accordance with the stimulation strategy by applying the stimulation only during time that corresponds to the stimulation frames,
   direct the sensing device to detect the physiological condition of the recipient in accordance with the stimulation strategy by detecting only during time that corresponds to the stimulation gaps, and
   perform an action based on the detected physiological condition.

2. The system of claim 1, wherein the characteristic of the recipient is a stimulation gap perception ability of the recipient that is determined by one or more of:
   receiving, from the recipient, behavioral input representative of the stimulation gap perception ability of the recipient; or
   automatically detecting, without behavioral input received by the recipient, the stimulation gap perception ability of the recipient.

3. The system of claim 1, further comprising:
   an additional sensing device configured to detect an additional physiological condition of the recipient, the additional physiological condition of a different physiological condition type than the physiological condition;
   wherein:
   the directing of the sensing device to detect the physiological condition includes directing the sensing device to detect the physiological condition only during time that corresponds to a first subset of the stimulation gaps,
   the processing unit is further communicatively coupled to the additional sensing device and is further configured to direct the additional sensing device to detect the additional physiological condition only during time that corresponds to a second subset of the stimulation gaps distinct from the first subset of the stimulation gaps.

4. The system of claim 1, wherein the stimulation gaps of the stimulation strategy are of uniform length and are periodically located throughout the stimulation strategy at set intervals of time.

5. The system of claim 1, wherein:
   the time that corresponds to the stimulation gaps during which the physiological condition is detected includes time corresponding to at least two stimulation gaps separated by at least one stimulation frame; and
   the detecting of the physiological condition includes combining data detected during each of the at least two stimulation gaps.

6. The system of claim 1, wherein the determining of the stimulation strategy includes customizing the stimulation strategy to the recipient based on a test applied to the recipient to automatically determine characteristics perceived by a brain of the recipient with respect to one or more prospective stimulation strategies presented to the recipient.

7. The system of claim 1, wherein the sensing device includes one or more of:
   an electrocardiogram (EKG) sensor for detecting a heart rate variability of the recipient;
   an electroencephalogram (EEG) sensor for detecting a brain wave pattern of the recipient;
   an electromyogram (EMG) sensor for detecting a muscle tissue function of the recipient;
   an electrooculogram (EOG) sensor for performing eye monitoring for the recipient;
   a photoplethysmogram (PPG) sensor for detecting blood volume changes in the recipient;
   a skin contact sensor for performing electrodiagnostic monitoring of the recipient; or
   an orientational sensor for detecting an orientation of the recipient.

8. The system of claim 1, wherein the detected physiological condition is a heart rate variability condition having an established correlation with a particular sentiment of the recipient.

9. The system of claim 1, wherein the stimulation device is configured to apply electrical or acoustic stimulation configured to evoke a hearing sense of the recipient.

10. The system of claim 9, further comprising a microphone configured to detect sound that is presented to the recipient;
    wherein:
    the detected physiological condition is that eyes of the recipient are looking in a particular direction; and
    the action performed based on the detected physiological condition is a beamforming action with respect to the microphone to focus the microphone in the particular direction that the eyes of the recipient are looking.

11. The system of claim 9, wherein:
the detected physiological condition is an average rate at which eyes of the recipient are blinking; and
the action performed based on the detected physiological condition is to adjust a noise reduction parameter of the system based on the average rate at which the eyes of the recipient are blinking.

12. The system of claim 9, wherein the stimulation device includes:
a hearing aid configured to be worn by the recipient on an ear of the recipient; and
a loudspeaker associated with the hearing aid and configured, when the hearing aid is worn by the recipient, to apply the acoustic stimulation to the recipient.

13. The system of claim 12, wherein:
the sensing device includes at least one sensor that is worn on the ear of the recipient and is sensitive to interference from at least one of the stimulation device and the processing unit; and
the directing of the sensing device to detect the physiological condition only during the time that corresponds to the stimulation gaps allows the sensing device to avoid the interference while performing the detecting of the physiological condition.

14. A method comprising:
determining, by a stimulation system including a stimulation device configured to apply stimulation to a recipient and a sensing device configured to detect a physiological condition of the recipient, a stimulation strategy that is customized to the recipient and includes stimulation frames and stimulation gaps, the determining of the stimulation strategy including:
identifying a type of physiological condition that is to be detected,
selecting, based on the identified type of physiological condition, a length of the stimulation frames and a length of the stimulation gaps, and
determining, based on the identified type of physiological condition and a characteristic of the recipient, a temporal pattern for the stimulation gaps and the stimulation frames;
directing, by the stimulation system, the stimulation device to apply the stimulation to the recipient in accordance with the stimulation strategy by applying the stimulation only during time that corresponds to the stimulation frames;
directing, by the stimulation system, the sensing device to detect the physiological condition of the recipient in accordance with the stimulation strategy by detecting only during time that corresponds to the stimulation gaps; and
performing, by the stimulation system, an action that is based on the detected physiological condition.

\* \* \* \* \*